United States Patent [19]

Doria et al.

[11] Patent Number: 4,816,467

[45] Date of Patent: Mar. 28, 1989

[54] HETEROARYL 3-OXO-PROPANENITRILE DERIVATIVES, PHARMACEUTICAL COMPOSITIONS AND USE

[75] Inventors: Gianfederico Doria, Milan; Anna M. Isetta, Rho; Mario Ferrari; Domenico Trizio, both of Milan, all of Italy

[73] Assignee: Farmitalia Carlo Erba s.r.l, Milan, Italy

[21] Appl. No.: 140,221

[22] Filed: Dec. 31, 1987

[30] Foreign Application Priority Data

Jan. 9, 1987 [GB] United Kingdom ................. 8700477
Jul. 22, 1987 [GB] United Kingdom ................. 8717282

[51] Int. Cl.4 ................... A61K 31/415; A61K 31/44; C07D 491/052; C07D 495/04
[52] U.S. Cl. ................... 514/333; 514/338; 514/403; 546/256; 546/271; 548/370
[58] Field of Search ............... 548/370; 514/407, 333, 514/338, 403; 546/279, 256, 271

[56] References Cited

U.S. PATENT DOCUMENTS 4,268,516 5/1981 Lombardino et al. ............. 548/359

Primary Examiner—Robert W. Ramsuer
Attorney, Agent, or Firm—Armstrong, Nikaido, Marmelstein & Kubovcik

[57] ABSTRACT

The invention relates to compounds having the general formula (I)

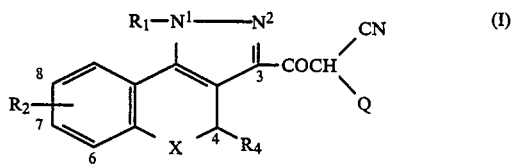

and the pharmaceutically acceptable salts thereof, which possess immunomodulating activity and are useful e.g. in the treatment of neoplastic diseases and acute and chronic infections of both bacterial and viral origin in mammals.

7 Claims, No Drawings

HETEROARYL 3-OXO-PROPANENITRILE DERIVATIVES, PHARMACEUTICAL COMPOSITIONS AND USE

The present invention relates to new heteroaryl 3-oxo-propanamide derivatives, to a process for their preparation and to pharmaceutical compositions containing them.

The compounds of the invention have the general formula (I)

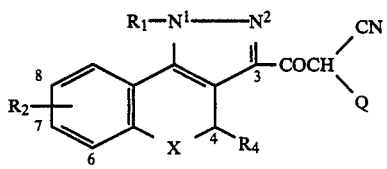

wherein

X represents an oxygen atom or a —S(O)$_n$-group, wherein n is zero, 1 or 2;

$R_1$ represents $C_1$–$C_6$ alkyl, benzyl, pyridyl or phenyl, the phenyl being unsubstituted or substituted by one or two substituents chosen independently from halogen, trifluoromethyl, $C_1$–$C_6$ alkyl, $C_1$–$C_6$ alkoxy, nitro, amino, formylamino and $C_2$–$C_8$ alkanoylamino;

each of $R_2$ and $R_3$ is independently:
  (a) hydrogen, halogen or $C_1$–$C_6$ alkyl;
  (b) hydroxy, $C_1$–$C_6$ alkoxy or $C_3$–$C_4$ alkenyloxy; or
  (c) nitro, amino, formylamino or $C_2$–$C_8$ alkanoylamino;

$R_4$ represents hydrogen or $C_1$–$C_6$ alkyl; and

Q represents hydrogen, carboxy, $CONH_2$, $C_2$–$C_7$ alkoxycarbonyl or a

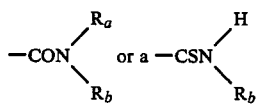

group, wherein $R_a$ represents hydrogen or $C_1$–$C_{20}$ alkyl and $R_b$ represents $C_1$–$C_{20}$ alkyl or a —(CH$_2$)$_m$—$R_5$ group, wherein m is zero, 1 or 2 and $R_5$ is:
  (a') $C_5$–$C_8$ cycloalkyl;
  (b') pyridyl, unsubstituted or substituted by one or two substituents chosen independently from halogen, $C_1$–$C_6$ alkyl and $C_1$–$C_6$ alkoxy; or
  (c') phenyl, unsubstituted or substituted by one or two substituents independently chosen from halogen, $CF_3$, $C_1$–$C_6$ alkyl, $C_1$–$C_6$ alkoxy, amino, nitro, formylamino, $C_2$–$C_8$ alkanoylamino, di($C_1$–$C_6$ alkyl)amino, hydroxy, formyloxy and $C_2$–$C_8$ alkanoyloxy.

The present invention includes within its scope the pharmaceutically acceptable salts, and also all possible isomers, stereoisomers and optical isomers and their mixtures, and the metabolites and the metabolic precursors or bioprecursors of the compounds of formula (I).

It has to be noticed that the compounds of formula (I) may be represented also by a tautomeric structure, namely the enol structure of formula (Ia)

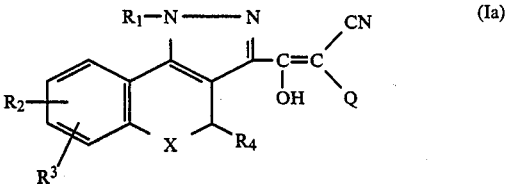

wherein

X, $R_1$, $R_2$, $R_3$, $R_4$ and Q are as defined above.

However, the compounds of formula (Ia), which fall within the scope of the present invention too, are described in the present specification as compounds of formula (I). A halogen atom is preferably chlorine or fluorine. The alkyl, alkanoyloxy, alkoxy and alkanoylamino groups may be branched or straight chain groups.

A $C_1$–$C_{20}$ alkyl group is preferably a $C_1$–$C_6$ alkyl group.

A $C_1$–$C_6$ alkyl group is, e.g., methyl, ethyl, propyl, isopropyl, butyl or tert.butyl, more preferably methyl or tert.butyl.

A $C_3$–$C_4$ alkenyloxy group is preferably allyloxy.

A $C_1$–$C_6$ alkoxy group is, e.g., methoxy, ethoxy, propoxy, isopropoxy, butoxy or tert.butoxy, preferably it is methoxy, ethoxy or propoxy.

A $C_5$–$C_8$ cycloalkyl group is preferably cyclopentyl or cyclohexyl.

A $C_2$–$C_8$ alkanoylamino group is preferably acetylamino or propionylamino.

A $C_2$–$C_8$ alkanoyloxy group is preferably acetoxy or propionyloxy.

A $C_2$–$C_7$ alkoxycarbonyl group is preferably a $C_2$–$C_5$ alkoxycarbonyl group, in particular a $C_2$–$C_3$ alkoxycarbonyl one. Examples of pharmaceutically acceptable salts are either those with inorganic bases, such a sodium, potassium, calcium and aluminium hydroxydes, or with organic bases, such as lysine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids. Preferred salts of the compounds of formula (I) are the sodium and the potassium salts thereof.

As stated above, the present invention also includes within its scope pharmaceutically acceptable bioprecursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are the compounds of formula (I), wherein X is oxygen or a —S(O)$_p$-group,
in which
p is zero or 1;
$R_1$ represents $C_1$–$C_6$ alkyl; unsubstituted pyridyl; or phenyl, unsubstituted or substituted by one or two substituents chosen independently from halogen, trifluoromethyl, $C_1$-$C_6$ alkyl, $C_1$-$C_6$ alkoxy, nitro, amino and $C_2$-$C_8$ alkanoylamino;

$R_2$ and $R_3$ each independently is hydrogen, halogen, $C_1$-$C_4$ alkyl or $C_1$-$C_4$ alkoxy;

$R_4$ represents hydrogen or $C_1$-$C_4$ alkyl;

Q represents hydrogen, —$CONH_2$, $C_2$-$C_5$ alkoxycarbonyl or a —$CONR'_aR'_b$ or —$CSNHR'_b$ group, wherein $R'_a$ is hydrogen or $C_1$-$C_6$ alkyl and $R'_b$ is $C_1$-$C_6$ alkyl or a —$(CH_2)_m$—$R'_5$ group wherein m is 0, 1 or 2 and $R'_5$ is $C_5$-$C_8$ cycloalkyl, unsubstituted pyridyl or phenyl unsubstituted or substituted by one or two substituents chosen independently from halogen, $CF_3$, $C_1$-$C_4$ alkyl, $C_1$-$C_4$ alkoxy, hydroxy, nitro and di-($C_1$-$C_4$ alkyl)amino; and the pharmaceutically acceptable salts thereof.

More preferred compounds of the invention are the compounds of formula (I) wherein X is oxygen or sulphur;

$R_1$ represents $C_1$-$C_4$ alkyl or phenyl unsubstituted or substituted by one or two substituents selected independently from nitro, halogen, $CF_3$, $C_1$-$C_4$ alkyl and $C_1$-$C_4$ alkoxy; each of $R_2$ and $R_3$ independently is hydrogen, halogen, $C_1$-$C_4$ alkyl or $C_1$-$C_4$ alkoxy;

$R_4$ represents hydrogen or $C_1$-$C_4$ alkyl;

Q represents hydrogen, $C_2$-$C_3$ alkoxycarbonyl or a —$CONR''_aR''_b$ or —$CSNHR''_b$ group wherein $R''_a$ is hydrogen or $C_1$-$C_4$ alkyl and $R''_b$ is $C_1$-$C_4$ alkyl or a —$(CH_2)_m$—$R''_5$ group in which m is as defined above and $R''_5$ is $C_5$-$C_6$ cycloalkyl or it is phenyl unsubstituted or substituted by one or two substituents chosen independently from nitro, halogen, $CF_3$, $C_1$-$C_4$ alkyl and $C_1$-$C_4$ alkoxy and the pharmaceutically acceptable salts thereof.

Examples of particularly preferred compounds of the invention are:

2-cyano-3-(1,4-dihydro-1-phenyl)-[1]-benzothiopyrano[4,3-c]pyrazol-3-yl)-3-oxo-N-phenyl-propanamide;

N-(3-chloro-phenyl)-2-cyano-3-(1,4-dihydro-1-phenyl-[1]-benzothiopyrano[4,3-c]pyrazol-3-yl)-3-oxo-propanamide;

2-cyano-3-(1,4-dihydro-1-phenyl-[1]-benzothiopyrano[4,3-c]pyrazol-3-yl)-3-oxo-N-(3-trifluoromethyl-phenyl)-propanamide;

2-cyano-3-(1,4-dihydro-1-phenyl-[1]-benzothiopyrano[4,3-c]pyrazol-3-yl)-N-(4-fluoro-phenyl)-3-oxo-propanamide;

3-(8-chloro-1,4-dihydro-1-phenyl-[1]-benzopyrano[4,3-c]pyrazol-3-yl)-2-cyano-N-(4-fluoro-phenyl)-3-oxo-propanamide;

N-(3,5-dichloro-phenyl)-2-cyano-3-(1,4-dihydro-1-phenyl-[1]-benzothiopyrano[4,3-c]pyrazol-3-yl)-3-oxo-propanamide;

N-benzyl-2-cyano-3-(1,4-dihydro-1-phenyl-[1]-benzothiopyrano[4,3-c]pyrazol-3-yl)-3-oxo-propanamide;

3-(8-chloro-1,4-dihydro-1-phenyl-[1]-benzothiopyrano[4,3-c]pyrazol-3-yl)-2-cyano-3-oxo-phenyl-propanamide;

2-cyano-3-(1,4-dihydro-8-methyl-1-phenyl-[1]-benzothiopyrano[4,3-c]pyrazol-3-yl)-3-oxo-N-phenyl-propanamide;

N-benzyl-3-(8-chloro-1,4-dihydro-1-phenyl-[1]-benzothiopyrano[4,3-c]pyrazol-3-yl)-2-cyano-3-oxo-propanamide;

N-benzyl-2-cyano-3-(1,4-dihydro-8-methyl-1-phenyl-[1]-benzothiopyrano[4,3-c]pyrazol-3-yl)-3-oxo-propanamide;

2-cyano-3-(1,4-dihydro-8-methoxy-1-phenyl-[1]-benzothiopyrano[4,3-c]pyrazol-3-yl)-3-oxo-N-phenyl-propanamide;

N-(3-chloro-phenyl)-3-(8-chloro-1,4-dihydro-1-phenyl-[1]-benzothiopyrano[4,3-c]pyrazol-3-yl)-2-cyano-3-oxo-propanamide;

N-benzyl-2-cyano-3-(1,4-dihydro-8-methoxy-1-phenyl-[1]-benzothiopyrano[4,3-c]pyrazol-3-yl)-3-oxo-propanamide;

3-(8-chloro-1,4-dihydro-1-phenyl-[1]-benzothiopyrano[4,3-c]pyrazol-3-yl)-2-cyano-N-(4-fluoro-phenyl)-3-oxo-propanamide;

3-[1-(4-fluoro-phenyl)-1,4-dihydro-[1]-benzothiopyrano[4,3-c]pyrazol-3-yl]-2-cyano-N-(4-fluoro-phenyl)-3-oxo-propanamide;

3-[1-(3,5-dichloro-phenyl)-1,4-dihydro-[1]-benzothiopyrano[4,3-c]pyrazol-3-yl]-2-cyano-3-oxo-N-phenyl-propanamide;

2-cyano-3-[1,4-dihydro-1-(4-fluoro-phenyl)-[1]-benzothiopirano[4,3-c]pyrazol-3-yl]-3-oxo-N-phenyl-propanamide;

N-benzyl-3-[1-(3-chloro-phenyl)-1,4-dihydro-[1]-benzothiopyrano[4,3-c]pyrazol-3-yl]-2-cyano-3-oxo-propanamide;

N-benzyl-3-[1-(3,5-dichloro-phenyl)-1,4-dihydro-[1]-benzothiopyrano[4,3-c]pyrazol-3-yl]-2-cyano-3-oxo-propanamide;

N-benzyl-2-cyano-3-[1-(4-fluoro-phenyl)-1,4-dihydro-[1]-benzothiopyrano[4,3-c]pyrazol-3-yl]-3-oxo-propanamide;

N-benzyl-3-[8-chloro-1-(4-fluoro-phenyl)-1,4-dihydro-[1]-benzothiopyrano[4,3-c]pyrazol-3-yl]-2-cyano-3-oxo-propanamide;

3-[8-chloro-1-(4-fluoro-phenyl)-1,4-dihydro-[1]-benzothiopyrano[4,3-c]pyrazol-3-yl]-2-cyano-3-oxo-N-phenyl-propanamide;

2-cyano-3-(1,4-dihydro-1-phenyl-[1]-benzopyrano[4,3-c]pyrazol-3-yl)-3-oxo-N-phenyl-propanamide;

N-(3-chloro-phenyl)-2-cyano-3-(1,4-dihydro-1-phenyl[1]-benzopyrano[4,3-c]pyrazol-3-yl)-3-oxo-propanamide;

2-cyano-3-(1,4-dihydro-1-phenyl-[1]-benzopyrano[4,3-c]pyrazol-3-yl)-N-(4-fluoro-phenyl)-3-oxo-propanamide;

N-benzyl-2-cyano-3-(1,4-dihydro-1-phenyl-[1]-benzopyrano[4,3-c]pyrazol-3-yl)-3-oxo-propanamide;

2-cyano-3-(1,4-dihydro-1-phenyl-[1]-benzothiopyrano[4,3-c]pyrazol-3-yl)-N-(3-fluoro-phenyl)-3-oxo-propanamide;

3-[1-(3-chloro-phenyl)-1,4-dihydro-[1]-benzopyrano[4,3-c]pyrazol-3-yl]-2-cyano-3-oxo-N-phenyl-propanamide;

2-cyano-3-[1,4-dihydro-1-(4-fluoro-phenyl)-[1]-benzopyrano[4,3-c]pyrazol-3-yl]-3-yl]-3-oxo-N-phenyl-propanamide;

N-benzyl-3-[1-(3-chloro-phenyl)-1,4-dihydro-[1]-benzopyrano[4,3-c]pyrazol-3-yl]-2-cyano-3-oxo-propanamide;

N-benzyl-2-cyano-3-[1-(4-fluoro-phenyl)-1,4-dihydro-[1]-benzopyrano[4,3-c]pyrazol-3-yl]-3-oxo-propanamide;

2-cyano-3-(1,4-dihydro-4-methyl-1-phenyl-[1]-benzopyrano[4,3-c]pyrazol-3-yl)-3-oxo-N-phenyl-propanamide;

N-benzyl-2-cyano-3-(1,4-dihydro-4-methyl-1-phenyl-[1]benzopyrano[4,3-c]pyrazol-3-yl)-3-oxo-propanamide;

3-(8-chloro-1,4-dihydro-1-phenyl-[1]-benzopyrano[4,3-c]pyrazol-3-yl)-2-cyano-3-oxo-N-phenyl-propanamide;

N-benzyl-3-(8-chloro-1,4-dihydro-1-phenyl-[1]-benzopyrano[4,3-c]pyrazol-3-yl)-2-cyano-3-oxo-propanamide;

3-(8-chloro-1,4-dihydro-1-phenyl[1]-benzothiopyrano[4,3-c]pyrazol-3-yl)-2-cyano-N-(3-fluoro-phenyl)-3-oxo-propanamide;

3-(8-chloro-1,4-dihydro-1-phenyl-[1]-benzopyrano[4,3-c]pyrazol-3-yl)-2-cyano-N-(3-fluoro-phenyl)-3-oxo-propanamide;

and the pharmaceutically acceptable salts thereof, in particular the sodium and the potassium salts.

The compounds of formula (I) and the salts thereof can be prepared by a process comprising:

(a) reacting a compound of formula (II)

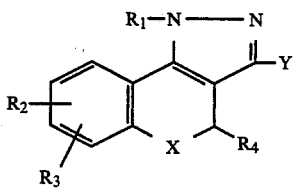 (II)

wherein X, R₁, R₂, R₃ and R₄ are as defined above and Y is carboxy or a reactive derivative of a carboxy group, with a compound of formula (III)

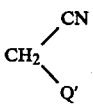 (III)

wherein Q is an Q defined above, except carboxy, so obtaining a compound of formula (I), wherein Q is as defined above except carboxy; or (b) reacting a compound of formula (IV)

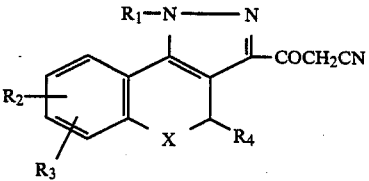 (IV)

wherein X, R₁, R₂, R₃ and R₄ are as defined above, with a compound formula (V) or (Va)

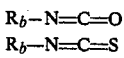 (V)
 (Va)

wherein $R_b$ is as defined above, so obtaining a compound of formula (I) wherein Q is a —CONHR$_b$ or a —CSNHR$_b$ group, respectively, wherein $R_b$ is as defined above; or (c) reacting a compound of formula (VI)

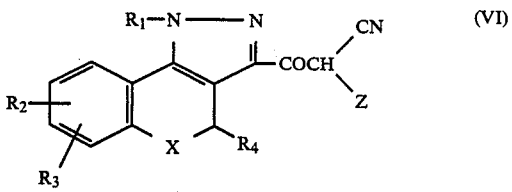 (VI)

wherein X, R₁, R₂, R₃ and R₄ are as defined above and Z is a reactive derivative of a carboxy group, with a compound of formula (VII)

 (VII)

wherein
$R_a$ and $R_b$ are as defined above, so obtaining compounds of formula (I) wherein
Q is a

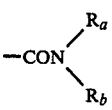

group, wherein $R_a$ and $R_b$ are as defined above; or (d) converting a compound of formula (I) wherein Q is a C₂–C₇ alkoxycarbonyl group into the corresponding compound of formula (I) in which Q is a free carboxy group; and, if desired, converting a compound of formula (I) into another compound of formula (I) and/or, if desired, converting a compound of formula (I) into a pharmaceutically acceptable salt and/or, if desired, converting a salt into a free compound.

When Y is a reactive derivative of a carboxy group, it is, for example, a halocarbonyl group, preferably a chlorocarbonyl group, or a C₂–C₇ alkoxycarbonyl group, preferably a C₂–C₃ alkoxycarbonyl group.

The reaction between a compound of formula (II) wherein Y is carboxy and a compound of formula (III) may be carried out, for example, in the presence of a condensing agent such as diethyl cyanophosphonate, in the presence of a base such as triethylamine, in an inert solvent such as dimethylformamide at a temperature varying between about 0° C. and about 50° C. The reaction between a compound of formula (II) wherein Y is a reactive derivative of a carboxy group and a compound of formula (III) may be carried out, for example, in the presence of a strong base such as sodium hydride, potassium t.butoxide, thallous ethoxide, in an inert solvent such as 1,2-dimethoxyethane, dioxane, dimethylformamide, at a temperature varying between about 0° C. and about 100° C.

The reaction between a compound of formula (IV) and a compound of formula (V) or (Va) may be carried out, for example, in the presence of a base such as sodium hydride or triethylamine, in an inert solvent such as toluene, dioxane, tetrahydrofuran, dimethylformamide, at a temperature varying between about 0° C. and about 100° C.

In the compounds of formula (VI), Z is, for example, a halocarbonyl group, preferably a chlorocarbonyl group, or a C₂–C₇ alkoxycarbonyl group, preferably a C₂–C₃ alkoxycarbonyl group.

The reaction between a compound of formula (VI), wherein Z is a halocarbonyl group, and a compound of formula (VII) may be carried out, for example, in an inert solvent such as dichloroethane, dioxane, dimethylformamide, in the presence of pyridine or triethylamine as acid acceptor, at a temperature varying between about 0° C. and about 100° C. The reaction between a compound of formula (VI), wherein Z is $C_1$–$C_6$ alkyl ester, and a compound of formula (VII) may be carried out, for example, by heating at the reflux temperature in an aromatic hydrocarbon such as toluene or xylene, preferably distilling off slowly together with the diluent the free $C_1$–$C_6$ alcohol generated during the reaction.

The conversion of a compound of formula (I) wherein Q is a $C_2$–$C_7$ alkoxycarbonyl group into the corresponding compound of formula (I) in which Q is a free carboxyl group may be performed by selective basic hydrolysis, using e.g. aqueous sodium or potassium hydroxide in a solvent such as dioxane or dimethylformamide at a temperature varying between about 0° C. and about 50° C.

A compound of formula (I) may be converted, as stated above, into another compound of formula (I) by known methods; for example, in a compound of formula (I) a nitro group may be converted into an amino group by treatment, for example, with stannous chloride in concentrated hydrochloric acid, using, if necessary, an organic cosolvent such as acetic acid, dioxane, tetrahydrofuran at a temperature varying between room temperature and about 100° C. Furthermore, for example, an amino group may be converted into a formylamino or a $C_2$–$C_8$ alkanoylamino group, for example by reacting with formic acid or with the suitable $C_2$–$C_8$ alkanoyl anhydride without any solvent or in an organic solvent such as dioxane, dimethylformamide, tetrahydofuran, usually in the presence of a base such as pyridine or triethylamine, at a temperature varying between 0° C. and about 100° C.

Process-variants (b) and (c) described above may be considered as examples of conversions of a compound of formula (I) into another compound of formula (I) too.

Also the optional salification of a compound of formula (I) as well as the conversion of a salt into the free compound and the separation of a mixture of isomers into the single isomers may be carried out by conventional methods.

The compounds of formula (II), wherein Y is a $C_2$–$C_7$ alkoxycarbonyl group, may be prepared, for example, by reacting a compound of formula (VIII)

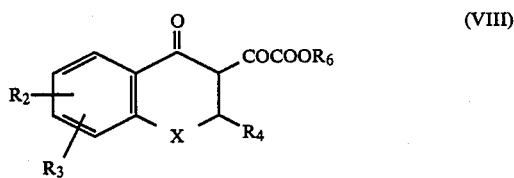

(VIII)

wherein X, $R_2$, $R_3$ and $R_4$ are as defined above and $R_6$ is $C_1$–$C_6$ alkyl, preferably $C_1$–$C_2$ alkyl, with a compound of formula (IX)

(IX)

wherein $R_1$ is as defined above.

The reaction between a compound of formula (VIII) and a compound of formula (IX) may be carried out, for example, in a solvent such as $C_1$–$C_6$ alkyl alcohol, dioxane, tetrahydrofuran, dimethylformamide, acetic acid, at a temperature varying between about 0° C. and about 150° C.

The compounds of formula (II), wherein Y is carboxy may be prepared, for example, by hydrolysis of the corresponding compounds of formula (II) wherein Y is $C_2$–$C_7$ alkoxycarbonyl, according to standard methods well known in the art, for example, by basic hydrolysis, carried out e.g. by treatment with sodium or potassium hydroxide in a solvent such as water, $C_1$–$C_6$ alkyl alcohol, dioxane, dimethylformamide and their mixtures, at a temperature varying between about 0° C. and about 50° C.

The compounds of formula (II), wherein Y is halocarbonyl, preferably chlorocarbonyl, may be prepared, for example, by reaction of the corresponding compound of formula (II), wherein Y is carboxy, with the suitable acid halide, for example oxalyl chloride, thionyl chloride, $PCl_3$, $PBr_3$, in an inert solvent such as ether, benzene, dichloroethane, dioxane or without any solvent, at a temperature varying between about 0° C. and about 100° C.

The compounds of formula (III) are, in some cases, commercially available products, or may be prepared by methods well known in the art. For example a compound of formula (III), wherein Q is a

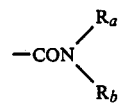

group, wherein $R_a$ and $R_b$ are as defined above, may be prepared by reacting cyanoacetic acid with a compound of formula (VII) in the presence of a condensing agent such as dicyclohexylcarbodiimide, 1,1-carbonyldiimidazole and the like, in an inert organic solvent such as benzene, dioxane, acetonitrile, at a temperature varying between about 0° C. and about 50° C.

The compounds of formula (IV) are compounds of general formula (I), wherein Q is hydrogen and may be obtained by process (a) above, for example, by reacting a compound of formula (II), wherein Y is $C_2$–$C_7$ alkoxycarbonyl, with acetonitrile, in the presence of a strong base e.g. sodium hydride, potassium tert.butoxide, in an inert organic solvent such as benzene, dioxane, tetrahydrofuran, at a temperature varying between about 0° C. and about 100° C.

The compounds of formula (VI), wherein Z is $C_2$–$C_7$ alkoxycarbonyl, are compounds of general formula (I) wherein Q is $C_2$–$C_7$ alkoxycarbonyl and may be obtained by process (a) above, for example, by reacting a compound of formula (II) with a compound of formula (X)

(X)

wherein $R_7$ is $C_1$–$C_6$ alkyl, using the same experimental conditions as described above for the reaction between a compound of formula (II) and a compound of formula (III).

The compounds of formula (VI), wherein Z is halocarbonyl, may be prepared, for example, by basic hydrolysis of a compound of formula (VI), wherein Z is $C_2$–$C_7$ alkoxycarbonyl, using, for example, the same experimental conditions described above for the hydrolysis of the compounds of formula (II), wherein Y is $C_2$–$C_7$ alkoxycarbonyl, in order to obtain the corresponding carboxy derivative, which in turn may be transformed into a compound of formula (VI), wherein Z is halocarbonyl, preferably chlorocarbonyl, using, for example, the same experimental conditions described above for the preparation of the compounds of formula (II), wherein Y is halocarbonyl.

The compounds of formula (VIII) may be prepared, for example, by reacting a compound of formula (XI)

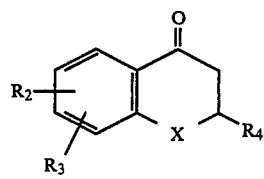
(XI)

wherein X, $R_2$, $R_3$ and $R_4$ are as defined above, with a compound of formula (XII)

(XII)

wherein each of $R_8$ and $R_8'$, being the same or different, is $C_1$–$C_6$ alkyl, preferably methyl or ethyl.

The reaction between a compound of formula (XI) and a compound of formula (XII) may be carried out, for example, in the presence of a strong base such as sodium methoxide, sodium ethoxide, sodium hydride, potassium tert.butoxide, in an organic solvent such as $C_1$–$C_6$ alkyl alcohol, benzene, dioxane, dimethylformamide, at a temperature varying between about 0° C. and about 100° C.

The compounds of formula (XI) may be prepared by synthetic methods well known in the art, for example, according to the methods described in J.A.C.S. 76, 5065 (1954) and in "Advances in Heterocyclic Chemistry", 18, 59 (1975).

The compounds of formula (V), (Va), (VII), (IX), (X) and (XII) are known products and may be prepared by conventional methods: in some cases they are commercially available products.

When in the compounds of the present invention and in the intermediate products thereof, groups are present, such as $NH_2$ and/or OH, which need to be protected before submitting them to the hereabove illustrated reactions, they may be protected before the reactions take place and then deprotected, according to well known methods in organic chemistry. The compounds of formula (I) possess immunomodulating activity and can be used in particular as immunostimulant agents e.g. in the treatment of acute and chronic infections of both bacterial and viral origin, alone or in association with antibiotic agents, and in the treatment of neoplastic diseases, alone or in association with antitumoral agents, in mammals.

The immunomodulating activity of the compounds of the invention is proved, for example, by the fact that they are effective in potentiating the cytotoxic activity of the macrophages towards tumor cells in vitro.

The experimental procedure to evaluate this activity is as follows: groups of 4 mice are treated i.p. with the tested compounds and then, seven days later, peritoneal cells are collected and plated for 2 hours at 37° C. After this period the walls are washed to eliminate the non adherent cells, tumor target cells are then added and the incubation is prolonged for 48 hours. At the end of this period the target cells viability is evaluated by a colorimetric method and quantified at 570 nm.

By virtue of their immunomodulating activity the compounds of the invention proved to be active also in models of infection in mice. The compound of the present invention 2-cyano-3-(1,4-dihydro-1-phenyl-[1]-benzothiopyrano[4,3-c]pyrazol-3-yl)-3-oxo-N-phenylpropanamide (internal code FCE 24578), for instance, was tested, according to the procedure described by Cleeland R., Grunberg E. 1986, 825–876, "Antibiotics in Laboratory Medicine" Lorian V. Editor (Williams and Wilkins), in the following models of infection: L. monocytogenes; D. pneumoniae; S. flexneri and P. aeruginosa; the last one being performed in cyclophosphamide immunosuppressed mice, according to Cryz S. J., Fürer E., Germanier R., 1983, Infect. Imm., 39, 1067–1071.

The following Tables 1, 2 and 3 summarize the obtained results:

TABLE 1

Activity of FCE 24578 on S. flexneri and D. pneumoniae infections in mice

| i.p. Treatment | | S. flexneri % mortality | D. pneumoniae MST (days) |
| --- | --- | --- | --- |
| FCE 24578 | 50 mg/kg | 10 | 5.7* |
| | 10 mg/kg | 40 | 4 |
| Controls | — | 100 | 3.1 |

Infection (3 × $LD_{50}$) was given i.p.
Treatments with FCE 24578 or vehicle were performed on −3, −2, −1 and 0 day before infection.
MST = Mean Survival Time.
* = significant for p < 0.01.

TABLE 2

Activity of FCE 24578 on L. monocytogenes infection in mice

| Treatment | | % mortality 1 × $LD_{50}$ |
| --- | --- | --- |
| FCE 24578 | 50 mg/kg i.p. | 0 |
| | 10 mg/kg i.p. | 12.5 |
| Controls | — | 75 |
| FCE 24578 | 250 mg/kg p.o. | 25 |
| | 50 mg/kg p.o. | 37.5 |
| Controls | — | 75 |

Treatments with FCE 2457B or vehicle were performed on −3, −2, −1 and 0 day before the infection (1 × $LD_{50}$) given i.v.

TABLE 3

Activity of FCE 24578 on P. aeruginosa infection in immunosuppressed mice

| i.p. Treatment | | % mortality 2 × $LD_{50}$ | 1 × $LD_{50}$ |
| --- | --- | --- | --- |
| FCE 24578 | 50 mg/kg | 0 | 0 |
| | 10 mg/kg | 0 | 0 |
| Controls | — | 90 | 80 |

Cyclophosphamide (200 mg/kg) was administered i.p. on the fourth day before infection.
The treatments with FCE 24578 or vehicle were performed on −3, −2, −1 and 0 day before the infection (2 × $LD_{50}$ and 1 × $LD_{50}$) given i.v.

As preferred examples of compounds of formula (I) having immunomodulating activity the following can be mentioned: 2-cyano-3-(1,4-dihydro-1-phenyl-[1]-benzopyrano[4,3-c]pyrazol-3-yl)-3-oxo-N-phenyl-propanamide (internal code FCE 25158) and 2-cyano-3-(1,4-dihydro-1-phenyl-[1]-benzothiopyrano[4,3-c]pyrazol-3- yl)-3-oxo-N-phenyl-propanamide (internal code FCE 24578). In view of their high therapeutic index the compounds of the invention can be safely used in medicine.

For example, the approximate acute toxicity ($LD_{50}$) in the mouse of the compounds 2-cyano-3-(1,4-dihydro-1-phenyl-[1]-benzopyrano[4,3-c]pyrazol-3-yl)-3-oxo-N-phenyl-propanamide, and 2-cyano-3-(1,4-dihydro-1-phenyl-[1]-benzothiopyrano[4,3-c]pyrazol-3-yl)-3-oxo-N-phenyl-propanamide, determined per os with single administration of increasing doses and measured on the seventh day after the day of treatment, is higher than 800 mg/kg. Analogous toxicity data have been found for the other compounds of the invention.

The therapeutic regimen for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the treatment of acute infections. For maintenance regimens the oral or parenteral, e.g. intramuscular or subcutaneous, route is preferred.

For these purposes the compounds of the invention can be administered orally at doses ranging e.g. from about 0.5 to about 10 mg/kg of body weight per day in adult humans. Doses of active compounds ranging e.g. from about 0.2 to about 5 mg/kg of body weight can be used for the parenteral administration in adult humans. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions or suspension, tablets, pills, gelatine capsules, syrups, drops or suppositories.

Thus, for oral administration, the pharmaceutical compositions containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The following examples illustrate but do not limit the invention:

EXAMPLE 1

Thiochroman-4-one (5 g) is reacted with diethyl oxalate (4.44 g) in anhydrous ethanol (25 ml) in the presence of sodium ethoxide (2.07 g) under stirring for 1 hour at about 10° C. and then for 3 hours at 25° C. The precipitate is filtered and washed with cold ethanol then dissolved in water. Acidification with citric acid gives an oil precipitate which is extracted with ethyl acetate. Evaporation of the solvent in vacuo to dryness gives 3-ethoxyalkyl-thiochroman-4-one, oil (5.65 g), which is reacted with phenylhydrazine (2.54 g) in acetic acid (35 ml) at a temperature varying between 25° C. and about 40° C. for 30 minutes. The reaction mixture is diluted with ice water and then neutralized with 30% ammonium hydroxide. The precipitate is filtered, dissolved in ethyl acetate and washed with water. After evaporation of the solvent in vacuo the residue is crystallized from dichloromethane/isopropyl ether to give 1,4-dihydro-1-phenyl-[1]-benzothiopyrano[4,3-c]pyrazole-3-carboxylic acid, ethyl ester, m.p. 139°–141° C. (4.2 g), which is reacted with acetonitrile (16.5 g) in dioxane (25 ml) in the presence of 50% sodium hydroxide (1.2 g) under stirring at 60° C. for 30 minutes. After cooling the reaction mixture is diluted with ice water and acidified to pH 4 with citric acid. The precipitate is filtered and washed with water and purified over a $SiO_2$ column using hexane-ethyl acetate 80:20 as eluent.

Crystallization from dichloromethane/isopropyl ether gives 3-(1,4-dihydro-1-phenyl-[1]-benzothiopyrano[4,3-c]pyrazol-3-yl)-3-oxo-propanenitrile, m.p. 151°–153° C. (3.45 g), which is reacted with phenyl isocyanate (1.3 g) in the presence of triethylamine (1.15 g) in dimethylformamide (30 ml) under stirring at 25°–30° C. for 30 minutes. The reaction mixture is diluted with ice water and the precipitate is filtered and washed with water. Crystallization from dichloromethane/methanol gives 4 g of 2-cyano-3-(1,4-dihydro-1-phenyl-[1]-benzothiopyrano[4,3-c]pyrazol-3-yl)-3-oxo-N-phenyl-propanamide, m.p. 228°–230° C., NMR (DMSO d 6) δppm: 4.20 (s) (2H, —$CH_2S$—), 6.60 (s) (1H, OH), 6.50–7.80 (m) (14H, phenyl protons), 10.90 (s) (1H, CONH—).

By proceeding analogously the following compounds can be prepared:

2-cyano-3-[1,4-dihydro-1-(4-methyl-phenyl)-[1]-benzothiopyrano[4,3-c]pyrazol-3-yl]-3-oxo-N-phenyl-propanamide, m.p. 262°–265° C.;

3-[1-(4-chloro-phenyl)-1,4-dihydro-[1]-benzothiopyrano[4,3-c]pyrazol-3-yl]-2-cyano-3-oxo-N-phenyl-propanamide, m.p. 235°–240° C. dec.;
2-cyano-3-[1,4-dihydro-1-(3-trifluoromethyl-phenyl)-[1]-benzothiopyrano[4,3-c]pyrazol-3-yl]-3-oxo-N-phenyl-propanamide;
3-[1-(3-chloro-phenyl)-1,4-dihydro-[1]-benzothiopyrano[4,3-c]pyrazol-3-yl]-2-cyano-3-oxo-N-phenyl-propanamide, m.p. 224°–226° C.
2-cyano-3-[1,4-dihydro-1-(4-fluoro-phenyl)-[1]-benzothiopyrano[4,3-c]pyrazol-3-yl]-3-oxo-N-phenyl-propanamide, m.p. 217°–218° C.;
3-[1-(2-chloro-phenyl)-1,4-dihydro-[1]-benzothiopyrano[4,3-c]pyrazol-3-yl]-2-cyano-3-oxo-N-phenyl-propanamide;
3-[1-(3,5-dichloro-phenyl)-1,4-dihydro-[1]-benzothiopyrano[4,3-c]pyrazol-3-yl]-2-cyano-3-oxo-N-phenyl-propanamide;
3-[1-(3-bromo-phenyl)-1,4-dihydro-[1]-benzothiopyrano[4,3-c]pyrazol-3-yl]-2-cyano-3-oxo-N-phenyl-propanamide;
2-cyano-3-[1,4-dihydro-1-(3-methyl-phenyl)-[1]-benzothiopyrano[4,3-c]pyrazol-3-yl]-3-oxo-N-phenyl-propanamide;
2-cyano-3-[1,4-dihydro-1-(3-nitro-phenyl)-[1]-benzothiopyrano[4,3-c]pyrazol-3-yl]-3-oxo-N-phenyl-propanamide;
2-cyano-3-[1,4-dihydro-1-(4-nitro-phenyl)-[1]-benzothiopyrano[4,3-c]pyrazol-3-yl]-3-oxo-N-phenyl-propanamide;
2-cyano-3-[1,4-dihydro-1-(4-methoxy-phenyl)-[1]-benzothiopyrano[4,3-c]pyrazol-3-yl]-3-oxo-N-phenyl-propanamide, m.p. 260° C. dec.;
2-cyano-3-[1,4-dihydro-1-(3-fluoro-phenyl)-[1]-benzothiopyrano[4,3-c]pyrazol-3-yl]-3-oxo-N-phenyl-propanamide; and
2-cyano-3-[1,4-dihydro-1-(3-methoxy-phenyl)-[1]-benzothiopyrano[4,3-c]pyrazol-3-yl]-3-oxo-N-phenyl-propanamide.

EXAMPLE 2

By proceeding according to Example 1, using the suitable substituted hydrazines, the following compounds can be prepared:
2-cyano-3-(1,4-dihydro-1-methyl-[1]-benzothiopyrano[4,3-c]pyrazol-3-yl)-3-oxo-N-phenyl-propanamide, m.p. 240°–242° C.;
3-(1-tert.butyl-1,4-dihydro-[1]-benzothiopyrano[4,3-c]pyrazol-3-yl)-2-cyano-3-oxo-N-phenyl-propanamide, m.p. 211°–212° C.;
2-cyano-3-(1,4-dihydro-1-ethyl-[1]-benzothiopyrano[4,3-c]pyrazol-3-yl)-3-oxo-N-phenyl-propanamide;
2-cyano-3-[1,4-dihydro-1-(2-pyridyl)-[1]-benzothiopyrano[4,3-c]pyrazol-3-yl]-3-oxo-N-phenyl-propanamide; and
2-cyano-3-[1,4-dihydro-1-(3-pyridyl)-[1]-benzothiopyrano[4,3-c]pyrazol-3-yl]-3-oxo-N-phenyl-propanamide.

EXAMPLE 3

By proceeding according to Examples 1 and 2, using the suitable isocyanates, the following compounds can be prepared:
N-(3-chloro-phenyl)-2-cyano-3-(1,4-dihydro-1-phenyl-[1]-benzothiopyrano[4,3-c]pyrazol-3-yl)-3-oxo-propanamide, m.p. 238°–240° C.;
N-(4-chloro-phenyl)-2-cyano-3-(1,4-dihydro-1-phenyl-[1]-benzothiopyrano[4,3-c]pyrazol-3-yl)-3-oxo-propanamide, m.p. 247°–249° C.;
2-cyano-3-(1,4-dihydro-1-phenyl-[1]-benzothiopyrano[4,3-c]pyrazol-3-yl)-N-(4-methoxy-phenyl)-3-oxo-propanamide, m.p. 219°–220° C.;
2-cyano-3-(1,4-dihydro-1-phenyl-[1]-benzothiopyrano[4,3-c]pyrazol-3-yl)-N-(4-methyl-phenyl)-3-oxo-propanamide, m.p. 217°–219° C.;
2-cyano-3-(1,4-dihydro-1-phenyl-[1]-benzothiopyrano[4,3-c]pyrazol-3-yl)-3-oxo-N-(3-trifluoromethyl-phenyl)-propanamide, m.p. 273°–277° C.;
2-cyano-3-(1,4-dihydro-1-phenyl-[1]-benzothiopyrano[4,3-c]pyrazol-3-yl)-N-(4-fluoro-phenyl)-3-oxo-propanamide, m.p. 260°–263° C.;
N-(3-chloro-phenyl)-2-cyano[1,4-dihydro-1-(4-fluoro-phenyl)-[1]-benzothiopyrano[4,3-c]pyrazol-3-yl]-3-oxo-propanamide;
3-[1-(4-fluoro-phenyl)-1,4-dihydro-[1]-benzothiopyrano[4,3-c]pyrazol-3-yl]-2-cyano-N-(4-fluoro-phenyl)-3-oxo-propanamide, m.p. 272° C. dec.;
N-(4-chloro-phenyl)-2-cyano-(1,4-dihydro-1-methyl-[1]-benzothiopyrano[4,3-c]pyrazol-3-yl)-3-oxo-propanamide;
3-[1-(3-chloro-phenyl)-1,4-dihydro-[1]-benzothiopyrano[4,3-c]pyrazol-3-yl]-N-(3-chloro-phenyl)-2-cyano-3-oxo-propanamide;
N-benzyl-2-cyano-[1,4-dihydro-1-(3-methoxy-phenyl)-[1]-benzothiopyrano[4,3-c]pyrazol-3-yl]-3-oxo-propanamide;
N-benzyl-2-cyano-[1,4-dihydro-1-(3-methyl-phenyl)-[1]-benzothiopyrano[4,3-c]pyrazol-3-yl]-3-oxo-propanamide;
N-(2-chloro-phenyl)-2-cyano-3-(1,4-dihydro-1-phenyl-[1]-benzothiopyrano[4,3-c]pyrazol-3-yl)-3-oxo-propanamide;
N-(3-bromo-phenyl)-2-cyano-3-(1,4-dihydro-1-phenyl-[1]-benzothiopyrano[4,3-c]pyrazol-3-yl)-3-oxo-propanamide;
2-cyano-3-(1,4-dihydro-1-phenyl-[1]-benzothiopyrano[4,3-c]pyrazol-3-yl)-N-(3-methyl-phenyl)-3-oxo-propanamide, m.p. 198°–200° C.;
2-cyano-3-(1,4-dihydro-1-phenyl-[1]-benzothiopyrano[4,3-c]pyrazol-3-yl)-N-(3-nitro-phenyl)-3-oxo-propanamide, m.p. 258°–261° C.;
3-[1-(3-chloro-phenyl)-1,4-dihydro-[1]-benzothiopyrano[4,3-c]pyrazol-3-yl]-2-cyano-N-(4-fluoro-phenyl)-3-oxo-propanamide;
3-[1-(3,5-dichloro-phenyl)-1,4-dihydro-[1]-benzothiopyrano[4,3-c]pyrazol-3-yl]-2-cyano-N-(4-fluoro-phenyl)-3-oxo-propanamide;
2-cyano-N-(4-fluoro-phenyl)-3-[1,4-dihydro-1-(3-trifluoromethyl-phenyl)-[1]-benzothiopyrano[4,3-c]pyrazol-3-yl]-3-oxo-propanamide;
N-benzyl-3-[1-(3-chloro-phenyl)-1,4-dihydro-[1]-benzothiopyrano[4,3-c]pyrazol-3-yl]-2-cyano-3-oxo-propanamide;
N-benzyl-3-[1(3,5-dichloro-phenyl)-1,4-dihydro-[1]-benzothiopyrano[4,3-c]pyrazol-3-yl]-2-cyano-3-oxo-propanamide;
N-benzyl-2-cyano-3-[1-(4-fluoro-phenyl)-1,4-dihydro-[1]-benzothiopyrano[4,3-c]pyrazol-3-yl]-3-oxo-propanamide;
N-benzyl-2-cyano-3-[1,4-dihydro-1-(3-trifluoromethyl-phenyl)-[1]-benzothiopyrano[4,3-c]pyrazol-3-yl]-3-oxo-propanamide;

N-benzyl-2-cyano-3-[1,4-dihydro-1-(3-nitro-phenyl)-[1]-benzothiopyrano[4,3-c]pyrazol-3-yl]-3-oxo-propanamide;

2-cyano-N-(3-fluoro-phenyl)-3-(1,4-dihydro-1-phenyl-[1]-benzothiopyrano[4,3-c]pyrazol-3-yl)-3-oxo-propanamide, m.p. 215°–217° C.;

N-butyl-2-cyano-3-(1,4-dihydro-1-phenyl-[1]-benzothiopyrano[4,3-c]pyrazol-3-yl)-3-oxo-propanamide, m.p. 208°–209° C.;

N-tert.butyl-2-cyano-3-(1,4-dihydro-1-phenyl-[1]-benzothiopyrano[4,3-c]pyrazol-3-yl)-3-oxo-propanamide;

N-butyl-3-[1-(3-chloro-phenyl)-1,4-dihydro-[1]-benzothiopyrano[4,3-c]pyrazol-3-yl]-2-cyano-3-oxo-propanamide;

N-tert.butyl-3-[1-(3-chloro-phenyl)-1,4-dihydro-[1]-benzothiopyrano[4,3-c]pyrazol-3-yl]-2-cyano-3-oxo-propanamide;

N-benzyl-2-cyano-3-(1,4-dihydro-1-phenyl-[1]-benzothiopyrano[4,3-c]pyrazol-3-yl)-3-oxo-propanamide, m.p. 268°–271° C.;

2-cyano-N-cyclohexyl-3-(1,4-dihydro-1-phenyl-[1]-benzothiopyrano[4,3-c]pyrazol-3-yl)-3-oxo-propanamide, m.p. 212°–214° C.; and 2-cyano-3-(1,4-dihydro-1-phenyl-[1]-benzothiopyrano[4,3-c]pyrazol-3-yl)-N-(3-methoxy-phenyl)-3-oxo-propanamide.

EXAMPLE 4

By proceeding according to Examples 1, 2 and 3, starting from the suitable thiochroman-4-one oxides, the following compounds can be prepared:

2-cyano-3-(1,4-dihydro-1-phenyl-[1]-benzothiopyrano[4,3-c]pyrazol-3-yl 5,5-dioxide)-3-oxo-N-phenyl-propanamide, m.p. 273°–275° C.;

N-(4-chloro-phenyl)-2-cyano-3-(1,4-dihydro-1-phenyl-[1]-benzothiopyrano[4,3-c]pyrazol-3-yl 5,5-dioxide)-3-oxo-propanamide;

2-cyano-3-(1,4-dihydro-1-phenyl-[1]-benzothiopyrano[4,3-c]pyrazol-3-yl 5-oxide)-3-oxo-N-phenyl-propanamide, and N-benzyl-2-cyano-3-(1,4-dihydro-1-phenyl-[1]-benzothiopyrano[4,3-c]pyrazol-3-yl 5-oxide)-3-oxo-propanamide.

EXAMPLE 5

1,4-Dihydro-1-phenyl-[1]-benzothiopyrano[4,3-c]pyrazole-3-carboxylic acid, ethyl ester (3.36 g) suspended in dioxane (60 ml) is treated with N/1 NaOH (30 ml) under stirring at room temperature for 5 hours. The reaction mixture is diluted with ice water and acidified to pH 3 with 37% HCl. The precipitate is filtered, washed with water and dried in vacuo at 50° C. to give 1,4-dihydro-1-phenyl-[1]-benzothiopyrano[4,3-c]pyrazole-3-carboxylic acid (2.8 g) which is reacted with oxalyl chloride (17 g) under stirring, at room temperature for 8 hours. The reaction mixture is evaporated to dryness in vacuo and the residue, 1,4-dihydro-1-phenyl-[1]-benzothiopyrano[4,3-c]pyrazole-3-carbonyl chloride (2.9 g), is dissolved in dimethylformamide (10 ml) and added under stirring to a suspension obtained by treatment of 2-cyano-acetylamino-pyridine (1.62 ) with 50% sodium hydride (0.5 g) in dimethylformamide (5 ml). The reaction mixture is kept at room temperature for 20 hours. The basic aqueous solution is washed with ethyl ether and then is acidified to pH 5 with 37% HCl. The precipitate is filtered, washed with water and then crystallized from ethanol to give 2.7 g of 2-cyano-3-(1,4-dihydro-1-phenyl-[1]-benzothiopyrano[4,3-c]pyrazol-3-yl)-3-oxo-N-(2-pyridyl)-propanamide, m.p. 258°–260° C.

By proceeding analogously the following compounds can be prepared:

2-cyano-3-(1,4-dihydro-1-phenyl-[1]-benzothiopyrano[4,3-c]pyrazol-3-yl)-3-oxo-N-(4-pyridyl)-propanamide;

2-cyano-N-(4-fluoro-benzyl)-3-(1,4-dihydro-1-phenyl-[1]-benzothiopyrano[4,3-c]pyrazol-3-yl)-3-oxo-propanamide;

2-cyano-3-(1,4-dihydro-1-phenyl-[1]-benzopyrano[4,3-c]pyrazol-3-yl)-3-oxo-N-(2-pyridyl)-propanamide;

2-cyano-3-(1,4-dihydro-1-phenyl-[1]-benzopyrano[4,3-c]pyrazol-3-yl)-3-oxo-N-(3-pyridyl)-propanamide;

2-cyano-3-(1,4-dihydro-1-phenyl-[1]-benzopyrano[4,3-c]pyrazol-3-yl)-3-oxo-N-phenyl-propanamide, m.p. 280°–282° C.;

2-cyano-3-(1,4-dihydro-1-phenyl-[1]-benzopyrano[4,3-c]pyrazol-3-yl)-3-oxo-N-methyl-N-(2-pyridyl)-propanamide;

2-cyano-3-(1,4-dihydro-1-phenyl-[1]-benzopyrano[4,3-c]pyrazol-3-yl)-3-oxo-N-methyl-N-phenyl-propanamide;

2-cyano-3-(1,4-dihydro-1-phenyl-[1]-benzothiopyrano[4,3-c]pyrazol-3-yl)-3-oxo-N-methyl-N-phenyl-propanamide, m.p. 183°–184° C.;

N-benzyl-2-cyano-3-[1-(3-fluoro-phenyl)-1,4-dihydro-[1]-benzothiopyrano[4,3-c]pyrazol-3-]-3-oxo-propanamide;

2-cyano-3-(1,4-dihydro-1-phenyl-[1]-benzothiopyrano[4,3-c]pyrazol-3-yl)-N-phenethyl-3-oxo-propanamide;

2-cyano-3-(1,4-dihydro-1-phenyl-[1]-benzothiopyrano[4,3-c]pyrazol-3-yl)-N-(4-dimethylamino-phenyl)-3-oxo-propanamide;

2-cyano-3-(1,4-dihydro-1-phenyl-[1]-benzothiopyrano[4,3-c]pyrazol-3-yl)-N-(2,6-dimethyl-phenyl)-3-oxo-propanamide, m.p. 215°–216° C.;

N-(3,5-dichloro-phenyl)-2-cyano-3-(1,4-dihydro-1-phenyl-[1]-benzothiopyrano[4,3-c]pyrazol-3-yl)-3-oxo-propanamide;

N-benzyl-2-cyano-3-(1,4-dihydro-1-phenyl-[1]-benzothiopyano[4,3-c]pyrazol-3-yl)-3-oxo-propanamide, mp. 268°–271° C.;

N-benzyl-2-cyano-3-(1,4-dihydro-1-phenyl-[1]-benzopyrano[4,3-c]pyrazol-3-yl)-3-oxo-propanamide;

N-(2-chloro-benzyl)-2-cyano-3-(1,4-dihydro-1-phenyl-[1]-benzothiopyrano[4,3-c]pyrazol-3-yl)-3-oxo-propanamide;

2-cyano-3-(1,4-dihydro-1-phenyl-[1]-benzothiopyrano[4,3-c]pyrazol-3-yl)-3-oxo-N-phenyl-propanamide, m.p. 228°–230° C.; and N-(3-hydroxy-phenyl)-2-cyano-3-(1,4-dihydro-1-phenyl-[1]-benzothiopyrano[4,3-c]pyrazol-3-yl)-3-oxo-propanamide; and N-benzyl-3-[1-(2-chloro-phenyl)-1,4-dihydro-[1]-benzothiopyrano[4,3-c]pyrazol-3-yl]-2-cyano-3-oxo-propanamide.

EXAMPLE 6

Ethyl cyanoacetate (1.4 g) is treated with 50% sodium hydride (0.58 g) in dimethylformamide (10 ml) under stirring at room temperature until the effervescence subsides. To this solution 1,4-dihydro-1-phenyl-[1]-benzothiopyrano[4,3-c]pyrazole-3-carbonyl chloride (3.26 g), prepared according to Example 5, dissolved in dimethylformamide (10 ml) is added under stirring at room temperature. The reaction mixture is allowed to react for 20 hours, then it is diluted with ice water and acidified to pH 3 with 37% HCl. The precipitate is extracted with ethyl acetate and the organic solution washed with water and then evaporated to dryness in vacuo. The residue is purified over a SiO$_2$ column, using hexane-ethyl acetate 80:20 as eluent, to give 2-cyano-3-(1,4-dihydro-1-phenyl-[1]-benzothiopyrano[4,3-c]pyrazol-3-yl)-3-oxo-propanoic acid, ethyl ester (2.4 g), m.p. 176°–178° C., which is reacted with aniline (1.7 g) in xylene (100 ml) at the reflux temperature for 48 hours. After cooling the precipitate is filtered and washed with xylene, then crystallized from dichloromethane/methanol to give 1.5 g of 2-cyano-3-(1,4-dihydro-1-phenyl-[1]-benzothiopyrano[4,3-c]pyrazol-3-yl)-3-oxo-N-phenyl-propanamide, m.p. 228°–230° C.

By proceeding analogously the following compounds can be prepared:

N-(3-chloro-phenyl)-2-cyano-3-(1,4-dihydro-1-phenyl-[1]-benzothiopyrano[4,3-c]pyrazol-3-yl)-3-oxo-propanamide, m.p. 238°–240° C.; and 2-cyano-3-(1,4-dihydro-1-phenyl-[1]-benzothiopyrano[4,3-c]pyrazol-3-yl)-3-oxo-N-(3-pyridyl)-propanamide.

EXAMPLE 7

By proceeding according to Examples 1 and 3, starting from the suitable substituted thiochroman-4-ones, the following compounds can be prepared:

2-cyano-3-(1,4-dihydro-8-methoxy-1-phenyl-[1]-benzothiopyrano[4,3-c]pyrazol-3-yl)-3-oxo-N-phenyl-propanamide, m.p. 205°–210° C. dec.;

3-(8-chloro-1,4-dihydro-1-phenyl-[1]-benzothiopyrano[4,3-c]pyrazol-3-yl)-2-cyano-3-oxo-N-phenyl-propanamide, m.p. 235°–236° C.;

2-cyano-3-(1,4-dihydro-8-methyl-1-phenyl-[1]-benzothiopyrano[4,3-c]pyrazol-3-yl)-3-oxo-N-phenyl-propanamide, mp. 224°–226° C.;

3-(7,8-dichloro-1,4-dihydro-1-phenyl-[1]-benzothiopyrano[4,3-c]pyrazol-3-yl)-2-cyano-3-oxo-N-phenyl-propanamide;

3-(8-bromo-1,4-dihydro-1-phenyl-[1]-benzothiopyrano[4,3-c]pyrazol-3-yl)-2-cyano-3-oxo-N-phenyl-propanamide;

N-benzyl-3-[8-chloro-1-(3-chloro-phenyl)-1,4-dihydro-[1]-benzothiopyrano[4,3-c]pyrazol-3-yl]-2-cyano-3-oxo-propanamide;

N-benzyl-3-[8-chloro-1-(4-fluoro-phenyl)-1,4-dihydro-[1]-benzothiopyrano[4,3-c]pyrazol-3-yl]-2-cyano-3-oxo-propanamide;

N-benzyl-3-(8-chloro-1,4-dihydro-1-phenyl-[1]-benzothiopyrano[4,3-c]pyrazol-3-yl)-2-cyano-3-oxo-propanamide, m.p. 216°–218° C.;

N-(3-chloro-phenyl)-3-(8-chloro-1,4-dihydro-1-phenyl-[1]-benzothiopyrano[4,3-c]pyrazol-3-yl)-2-cyano-3-oxo-propananide;

N-benzyl-3-[8-chloro-1-(3-fluoro-phenyl)-1,4-dihydro-[1]-benzothiopyrano[4,3-c]pyrazol-3-yl]-2-cyano-3-oxo-propanamide;

N-benzyl-3-[8-chloro-1,4-dihydro-1-(3-methyl-phenyl)-[1]-benzothiopyrano[4,3-c]pyrazol-3-yl]-2-cyano-3-oxo-propanamide;

3-(8-chloro-1,4-dihydro-1-phenyl-[1]-benzothiopyrano[4,3-c]pyrazol-3-yl)-2-cyano-3-oxo-N-(3-methyl-phenyl)-propanamide;

N-benzyl-2-cyano-3-(1,4-dihydro-8-methoxy-1-phenyl-[1]-benzothiopyrano[4,3-c]pyrazol-3-yl)-3-oxo-propanamide;

N-benzyl-2-cyano-3-(1,4-dihydro-8-methyl-1-phenyl-[1]-benzothiopyrano[4,3-c]pyrazol-3-yl)-3-oxo-propanamide;

3-[8-chloro-1-(3-chloro-phenyl)-1,4-dihydro-[1]-benzothiopyrano[4,3-c]pyrazol-3-yl]-2-cyano-3-oxo-N-phenyl-propanamide;

3-[8-chloro-1-(4-fluoro-phenyl)-1,4-dihydro-1[1]-benzothiopyrano[4,3-c]pyrazol-3-yl]-2-cyano-3-oxo-N-phenyl-propanamide;

N-(3-chloro-phenyl)-2-cyano-3-(1,4-dihydro-8-methyl-1-phenyl-[1]-benzothiopyrano[4,3-c]pyrazol-3-yl)-3-oxo-propanamide;

3-(8-chloro-1,4-dihydro-1-phenyl-[1]-benzothiopyrano[4,3-c]pyrazol-3-yl)-2-cyano-N-(4-fluoro-phenyl)-3-oxo-propanamide; and 3-(8-chloro-1,4-dihydro-1-phenyl-[1]-benzothiopyrano[4,3-c]pyrazol-3-yl)-2-cyano-N-(3-fluoro-phenyl)-3-oxo-propanamide.

EXAMPLE 8

2-Cyano-3-[1,4-dihydro-1-(3-nitro-phenyl)-[1]-benzothiopyrano[4,3-c]pyrazol-3-yl]-3-oxo-N-phenyl-propanamide (4.95 g) is reacted with SnCl$_2$.2H$_2$O (22.5 g) in 37% HCl (16 ml) and acetic acid (144 ml) under stirring at 40° C. for 5 hours. After cooling the precipitate is filtered and washed with acetic acid and then dissolved in dimethylformamide-2N NaOH 1:1. Dilution with excess aqueous NaH$_2$PO$_4$ gives a precipitate which is filtered, washed with water and crystallized from chloroform/ethanol to give 3.45 g of 3-[1-(3-amino-phenyl)-1,4-dihydro-[1]-benzothiopyrano[4,3-c]pyrazol-3-yl]-2-cyano-3-oxo-N-phenyl-propanamide.

By proceeding analogously the following compounds can be obtained:

3-[1-(4-amino-phenyl)-1,4-dihydro-[1]-benzothiopyrano[4,3-c]pyrazol-3-yl]-2-cyano-3-oxo-N-phenyl-propanamide;

3-(8-amino-1,4-dihydro-phenyl-[1]-benzopyrano[4,3-c]pyrazol-3-yl)-2-cyano-3-oxo-N-phenyl-propanamide; and N-(3-amino-phenyl)-2-cyano-3-(1,4-dihydro-1-phenyl-[1]-benzothiopyrano[4,3-c]pyrazol-3-yl)-3-oxo-propanamide.

EXAMPLE 9

3-[1-(3-amino-phenyl)-1,4-dihydro-[1]-benzothiopyrano[4,3-c]pyrazol-3-yl]-2-cyano-3-oxo-N-phenyl-propanamide (1.9 g) dissolved in dimethylformamide (25 ml) is reacted with acetic anhydride (5 ml) in the presence of pyridine (5 ml) at room temperature for 20 hours. The reaction mixture is diluted with ice water and the precipitate is filtered and washed with water: crystallization from dimethylformamide-ethanol gives 1.6 g of 3-[1-(3-acetylamino-)phenyl]-1,4-dihydro-[1]-benzothiopyrano[4,3-c]pyrazol-3-yl]-2-cyano-3-oxo-N-phenyl-propanamide.

By proceeding analogously the following compounds can be prepared:

3-[1-(4-acetylamino-phenyl)-1,4-dihydro-[1]-benzothiopyrano[4,3-c]pyrazol-3-yl]-2-cyano-3-oxo-N-phenyl-propanamide;

3-(8-acetylamino-1,4-dihydro-1-phenyl-[1]-benzopyrano[4,3-c]pyrazol-3-yl)-2-cyano-3-oxo-N-phenyl-propanamide; and N-(3-acetylamino-phenyl)-2-cyano-3-(1,4-dihydro-1-phenyl-[1]-benzothiopyrano[4,3-c]pyrazol-3-yl)-3-oxo-propanamide.

EXAMPLE 10

A solution of 4-chromanone (11.2 g) and diethyl oxalate (13.3 g) in anhydrous dioxane (75 ml) is added under stirring at room temperature to a suspension of 50% sodium hydride (4 g) in anhydrous dioxane (150 ml). The mixture is allowed to react under stirring at 80° C. for 3.5 hours. After cooling, the reaction mixture is diluted with ice water and acidified to pH 4 with 40% citric acid aqueous solution. The oily precipitate is extracted with ethyl acetate, then the organic solution is washed with 40% citric acid and water until neutral. After evaporation of the solvent in vacuo the residue is purified over a $SiO_2$ column using hexane/ethyl acetate 80:20 as eluent. Crystallization from isopropyl alcohol gives 3-ethoxalylchroman-4-one, m.p. 73°–75° C. (7.7 g), which is reacted with phenylhydrazine (3.68 g) in acetic acid (80 ml) at a temperature varying between 25° C. and about 40° C. for 30 minutes. The reaction mixture is diluted with ice water and then neutralized with 30% ammonium hydroxide. The precipitate is filtered and washed with water. Crystallization from isopropyl alcohol gives 1,4-dihydro-1-phenyl-[1]-benzopyrano[4,3-c]pyrazole-3-carboxylic acid, ethyl ester, m.p. 154°–156° C. (7.4 g), which is reacted with acetonitrile (74 ml) in dioxane (45 ml) in the presence of 50% sodium hydride (2.2 g) under stirring at 60° C. for 30 minutes. After cooling the reaction mixture is diluted with ice water and acidified to pH 4 with citric acid. The precipitate is filtered and washed with water and purified over a $SiO_2$ column, using chloroform as eluent.

Crystallization from dichloromethane/isopropyl ether gives 4.3 g of 3-(1,4-dihydro-1-phenyl-[1]-benzopyrano[4,3-c]pyrazol-3-yl)-3-oxo-propanenitrile, m.p. 155°–158° C., NMR ($CDCl_3$) δppm: 4.19 (s) (2H, —$CH_2CN$), 5.54 (s), (2H, —$OCH_2$—), 6.65–7.35 (m) (4H, benzopyran protons), 7.58 (m) (5H, phenyl protons).

By proceeding analogously the following compounds can be prepared:
3-[1-(4-chloro-phenyl)-1,4-dihydro-[1]-benzopyrano[4,3-c]pyrazol-3-yl]-3-oxo-propanenitrile;
3-[1-(3-chloro-phenyl)-1,4-dihydro-[1]-benzopyrano[4,3-c]pyrazol-3-yl]-3-oxo-propanenitrile;
3-[1,4-dihydro-1-(3-trifluoromethyl-phenyl)-[1]-benzopyrano[4,3-c]pyrazol-3-yl]-3-oxo-propanenitrile;
3-[1,4-dihydro-1-(3-nitro-phenyl)-[1]-benzopyrano[4,3-c]pyrazol-3-yl]-3-oxo-propanenitrile;
3-[1-(4-fluoro-phenyl)-1,4-dihydro-[1]-benzopyrano[4,3-c]pyrazol-3-yl]-3-oxo-propanenitrile;
3-[1,4-dihydro-1-(4-methyl-phenyl)-[1]-benzopyrano[4,3-c]pyrazol-3-yl]-3-oxo-propanenitrile;
3-[1,4-dihydro-1-(4-methoxy-phenyl)-[1]-benzopyrano[4,3-c]pyrazol-3-yl]-3-oxo-propanenitrile;
3-(1,4-dihydro-4-methyl-1-phenyl]-1]-benzopyrano[4,3-c]pyrazol-3-yl)-3-oxo-propanenitrile;
3-(1,4-dihydro-8-methyl-1-phenyl-[1]-benzopyrano[4,3-c]pyrazol-3-yl)-3-oxo-propanenitrile;
3-(1,4-dihydro-8-methoxy-1-phenyl-[1]-benzopyrano[4,3-c]pyrazol-3-yl)-3-oxo-propanenitrile;
3-(8-chloro-1,4-dihydro-1-phenyl-[1]-benzopyrano[4,3-c]pyrazol-3-yl)-3-oxo-propanenitrile;
3-(7,8-dichloro-1,4-dihydro-1-phenyl-[1]-benzopyrano[4,3-c]pyrazol-3-yl)-3-oxo-propanenitrile; and
3-(6,8-dichloro-1,4-dihydro-1-phenyl-[1]-benzopyrano[4,3-c]pyrazol-3-yl)-3-oxo-propanenitrile.

EXAMPLE 11

By proceeding according to Example 10, starting from suitable thiochroman-4-ones, the following compounds can be prepared:
3-[1,4-dihydro-1-(4-methyl-phenyl)-[1]-benzothiopyrano[4,3-c]pyrazol-3-yl]-3-oxo-propanenitrile, m.p. 183°–184° C.;
3-[1-(4-chloro-phenyl)-1,4-dihydro-[1]-benzothiopyrano[4,3-c]pyrazol-3-yl]-3-oxo-propanenitrile, m.p. 194°–198° C.;
3-[1,4-dihydro-1-(3-trifluoromethyl-phenyl)-[1]-benzothiopyrano[4,3-c]pyrazol-3-yl]-3-oxo-propanenitrile;
3-[1-(3-chloro-phenyl)-1,4-dihydro-[1]-benzothiopyrano[4,3-c]pyrazol-3-yl]-3-oxo-propanenitrile, m.p. 187°–188° C.;
3-[1,4-dihydro-1-(4-fluoro-phenyl)-[1]-benzothiopyrano[4,3-c]pyrazol-3-yl]-3-oxo-propanenitrile, m.p. 190°–192° C.;
3-[1,4-dihydro-1-(4-nitrophenyl)-[1]-benzothiopyrano[4,3-c]pyrazol-3-yl]-3-oxo-propanenitrile;
3-[1,4-dihydro-1-(4-methoxy-phenyl)-[1]-benzothiopyrano[4,3-c]pyrazol-3-yl]-3-oxo-propanenitrile, m.p. 157°–159° C.;
3-[1,4-dihydro-1-methyl-[1]-benzothiopyrano[4,3-c]pyrazol-3-yl]-3-oxo-propanenitrile, m.p. 188°–190° C.;
3-(1-tert.butyl-1,4-dihydro-[1]-benzothiopyrano[4,3-c]pyrazol-3-yl]-3-oxo-propanenitrile, m.p. 150°–152° C.;
3-(8-chloro-1,4-dihydro-1-phenyl-[1]-benzothiopyrano[4,3-c]-pyrazol-3-yl)-3-oxo-propanenitrile, m.p. 151°–153° C.;
3-(1,4-dihydro-8-methyl-1-phenyl-[1]-benzothiopyrano[4,3-c]pyrazol-3-yl)-3-oxo-propanenitrile;
3-(1,4-dihydro-8-methoxy-1-phenyl-[1]-benzothiopyrano[4,3-c]pyrazol-3-yl)-3-oxo-propanenitrile; and
3-(1,4-dihydro-1-phenyl-[1]-benzothiopyrano[4,3-c]pyrazol-3-yl)-3-oxo-propanenitrile, m,p. 151°–153° C.

EXAMPLE 12

3-(1,4-dihydro-1-phenyl-[1]-benzopyrano[4,3-c]pyrazol-3-yl)-3-oxo-propanenitrile (2.1 g) is reacted with phenyl isocyanate (0.8 g) in the presence of triethylamine (0.75 g) in dimethylformamide (20 ml) under stirring at 25°–30° C. for 90 minutes. The reaction mixture is diluted with ice water, acidified to pH 2 with HCl and the precipitate is filtered and washed with water. Crystallization from dichloromethane/methanol gives 2.5 g of 2-cyano-3-(1,4-dihydro-1-phenyl-[1]-benzopyrano[4,3-c]pyrazol-3-yl)-3-oxo-N-phenyl-propanamide, m.p. 280°–282° C., NMR ($CDCl_3$) δppm: 5.54 (s) (2H, —$CH_2O$—), 6.7–7.7 (m) (14H, phenyl protons), 8.94 (s) (1H, CONH—), 16.4 (bs) (1H, enol).

By proceeding analogously the following compounds can be prepared:
2-cyano-3-[1,4-dihydro-1-(3-nitrophenyl)-[1]-benzopyrano[4,3-c]pyrazol-3-yl]-3-oxo-N-phenyl-propanamide;

2-cyano-3-[1,4-dihydro-1-(3-methoxy-phenyl)-[1]-benzopyrano[4,3-c]pyrazol-3-yl]3-oxo-N-phenyl-propanamide;

2-cyano-3-[1,4-dihydro-1-(3-methyl-phenyl)-[1]-benzopyrano[4,3-c]pyrazol-3-yl]-3-oxo-N-phenyl-propanamide;

3-[1-(3-fluoro-phenyl)-1,4-dihydro-[1]-benzopyrano[4,3-c]pyrazol-3-yl]-2-cyano-3-oxo-N-phenyl-propanamide;

2-cyano-3-[1,4-dihydro-1-(3-trifluoromethyl-phenyl)-[1]-benzopyrano[4,3-c]pyrazol-3-yl]-3-oxo-N-phenyl-propanamide;

2-cyano-3-(1,4-dihydro-8-nitro-1-phenyl-[1]-benzopyrano[4,3-c]pyrazol-3-yl)-3-oxo-N-phenyl-propanamide;

3-(8-tert.butyl-1,4-dihydro-1-phenyl-[1]-benzopyrano[4,3-c]pyrazol-3-yl)-2-cyano-3-oxo-N-phenyl-propanamide;

3-(8-chloro-1,4-dihydro-1-phenyl-[1]-benzopyrano[4,3-c]pyrazol-3-yl)-2-cyano-3-oxo-N-phenyl-propanamide, m.p. 270°–273° C.;

3-(8-chloro-1,4-dihydro-4-methyl-1-phenyl-[1]-benzopyrano[4,3-c]pyrazol-3-yl)-2-cyano-3-oxo-N-phenyl-propanamide;

3-(7-chloro-1,4-dihydro-1-phenyl-[1]-benzopyrano[4,3c]pyrazol-3-yl)-2-cyano-3-oxo-N-phenyl-propanamide;

3-(6-chloro-1,4-dihydro-1-phenyl-[1]-benzopyrano[4,3-c]pyrazol-3-yl)-2-cyano-3-oxo-N-phenyl-propanamide;

3-(8-bromo-1,4-dihydro-1-phenyl-[1]-benzopyrano[4,3-c]pyrazol-3-yl)-2-cyano-3-oxo-N-phenyl-propanamide;

2-cyano-3-(1,4-dihydro-6,8-dimethyl-1-phenyl-[1]-benzopyrano[4,3-c]pyrazol-3-yl)-3-oxo-N-phenyl-propanamide;

3-[8-chloro-1-(3-chloro-phenyl)-1,4-dihydro-[1]-benzopyrano[4,3-c]pyrazol-3-yl]-2-cyano-3-oxo-N-phenyl-propanamide;

3-[8-chloro-1-(4-fluoro-phenyl)-1,4-dihydro-[1]-benzopyrano[4,3-c]pyrazol-3-yl]-2-cyano-3-oxo-N-phenyl-propanamide;

3-[1-(3-chloro-phenyl)-1,4-dihydro-[1]-benzopyrano[4,3-c]pyrazol-3-yl]-2-cyano-3-oxo-N-phenyl-propanamide;

2-cyano-3-[1,4-dihydro-1-(4-fluoro-phenyl)-[1]-benzopyrano[4,3-c]pyrazol-3-yl]-3-oxo-N-phenyl-propanamide;

2-cyano-3-(1,4-dihydro-8-methoxy-1-phenyl-[1]-benzopyrano[4,3-c]pyrazol-3-yl)-3-oxo-N-phenyl-propanamide;

3-(8-chloro-1,4-dihydro-1-phenyl-[1]-benzopyrano[4,3-c]pyrazol-3-yl)-2-cyano-3-oxo-N-phenyl-propanamide;

2-cyano-3-(1,4-dihydro-4-methyl-1-phenyl-[1]-benzopyrano[4,3-c]pyrazol-3-yl)-3-oxo-N-phenyl-propanamide, m.p. 243°–246° C.;

2-cyano-3-(7,8-dichloro-1,4-dihydro-1-phenyl-[1]-benzopyrano[4,3-c]pyrazol-3-yl)-3-oxo-N-phenyl-propanamide;

3-(6,8-dichloro-1,4-dihydro-1-phenyl-[1]-benzopyrano[4,3-c]pyrazol-3-yl)-2-cyano-3-oxo-N-phenyl-propanamide; and 2-cyano-3-(1,4-dihydro-8-methyl-1-phenyl-[1]-benzopyrano[4,3-c]pyrazol-3-yl)-3-oxo-N-phenyl-propanamide.

EXAMPLE 13

By proceeding according to Example 12, using the suitable isocyanates, the following compounds can be prepared;

N-(3-chloro-phenyl)-2-cyano-3-(1,4-dihydro-1-phenyl-[1]-benzopyrano[4,3-c]pyrazol-3-yl)-3-oxo-propanamide;

N-(3-fluoro-phenyl)-2-cyano-3-(1,4-dihydro-1-phenyl-[1]-benzopyrano[4,3-c]pyrazol-3-yl)-3-oxo-propanamide;

2-cyano-3-(1,4-dihydro-1-phenyl-[1]-benzopyrano[4,3-c]pyrazol-3-yl)-N-(3-methoxy-phenyl)-3-oxo-propanamide;

2-cyano-3-(1,4-dihydro-1-phenyl-[1]-benzopyrano[4,3-c]pyrazol-3-yl)-N-(3-methyl-phenyl)-3-oxo-propanamide;

2-cyano-3-(1,4-dihydro-1-phenyl-[1]-benzopyrano[4,3-c]pyrazol-3-yl)-3-oxo-N-(3-trifluoromethyl-phenyl)-propanamide;

2-cyano-3-(1,4-dihydro-1-phenyl-[1]-benzopyrano[4,3-c]pyrazol-3-yl)-N-(4-fluoro-phenyl)-3-oxo-propanamide;

3-[1-(4-chloro-phenyl)-1,4-dihydro-[1]-benzopyrano[4,3-c]pyrazol-3-yl]-2-cyano-N-(4-fluoro-phenyl)-3-oxo-propanamide;

2-cyano-3-(1,4-dihydro-1-phenyl-[1]-benzopyrano[4,3-c]pyrazol-3-yl)-N-(3-methyl-phenyl)-3-oxo-propanamide;

N-benzyl-2-cyano-3-(1,4-dihydro-8-methoxy-1-phenyl-[1]-benzopyrano[4,3-c]pyrazol-3-yl)-3-oxo-propanamide;

3-(8-chloro-1,4-dihydro-1-phenyl-[1]-benzopyrano[4,3-c]pyrazol-3-yl)-2-cyano-N-(3-fluoro-phenyl)-3-oxo-propanamide;

N-benzyl-2-cyano-3-(1,4-dihydro-1-phenyl-[1]-benzopyrano[4,3-c]pyrazol-3-yl)-3-oxo-propanamide;

2-cyano-N-cyclohexyl-3-(1,4-dihydro-1-phenyl-[1]-benzopyrano[4,3-c]pyrazol-3-yl)-3-oxo-propanamide;

2-cyano-3-(1,4-dihydro-1-phenyl-[1]-benzopyrano[4,3-c]pyrazol-3-yl)-N-methyl-3-oxo-propanamide;

2-cyano-N-ethyl-3-(1,4-dihydro-1-phenyl-[1]-benzopyrano[4,3-c]pyrazol-3-yl)-3-oxo-propanamide;

N-butyl-2-cyano-3-(1,4-dihydro-1-phenyl-[1]-benzopyrano[4,3-c]pyrazol-3-yl)-3-oxo-propanamide;

N-tert.butyl-2-cyano-3-(1,4-dihydro-1-phenyl-[1]-benzopyrano[4,3-c]pyrazol-3-yl)-3-oxo-propanamide;

N-(3,5-dichloro-phenyl)-2-cyano-3-(1,4-dihydro-1-phenyl-[1]-benzopyrano[4,3-c]pyrazol-3-yl)-3-oxo-propanamide;

2-cyano-3-(1,4-dihydro-1-phenyl-[1]-benzopyrano[4,3-c]pyrazol-3-yl)-N-(3-nitro-phenyl)-3-oxo-propanamide;

N-benzyl-2-cyano-3-[1-(4-fluoro-phenyl)-1,4-dihydro-[1]-benzopyrano[4,3-c]pyrazol-3-yl]-3-oxo-propanamide;

N-benzyl-3-(8-tert.butyl-1,4-dihydro-1-phenyl-[1]-benzopyrano[4,3-c]pyrazol-3-yl)-2-cyano-3-oxo-propanamide;

N-benzyl-3-(8-chloro-1,4-dihydro-1-phenyl-[1]-benzopyrano[4,3-c]pyrazol-3-yl)-2-cyano-3-oxo-propanamide, m.p. 281°–284° C.;

N-benzyl-3-[8-chloro-1-(3-chloro-phenyl)-1,4-dihydro-[1]-benzopyrano[4,3-c]pyrazol-3-yl]-2-cyano-3-oxo-propanamide;

N-benzyl-3-[8-chloro-1-(4-fluoro-phenyl)-1,4-dihydro-[1]-benzopyrano[4,3-c]pyrazol-3yl]-2-cyano-3-oxo-propanamide;

N-benzyl-2-cyano-3-(1,4-dihydro-8-methyl-1-phenyl-[1]-benzopyrano[4,3-c]pyrazol-3-yl)-3-oxo-propanamide;

N-(3-chloro-phenyl)-3-[1-(3-chloro-phenyl)-1,4-dihydro-[1]-benzopyrano[4,3-c]pyrazol-3-yl]-2-cyano-3-oxo-propanamide;

N-(3-chloro-phenyl)-3-[8-chloro-1,4-dihydro-1-phenyl-[1]-benzopyrano[4,3-c]pyrazol-3-yl]-2-cyano-3-oxo-propanamide;

N-(3-chloro-phenyl)-2-cyano-3-[1-(4-fluoro-phenyl)-1,4-dihydro-[1]-benzopyrano[4,3-c]pyrazol-3-yl]-3-oxo-propanamide;

3-[1-(3-chloro-phenyl)-1,4-dihydro-[1]-benzopyrano[4,3-c]pyrazol-3-yl]-2-cyano-N-(4-fluoro-phenyl)-3-oxo-propanamide;

2-cyano-3-[1-(4-fluoro-phenyl)-1,4-dihydro-[1]-benzopyrano[4,3-c]pyrazol-3-yl]-N-(4-fluoro-phenyl)-3-oxo-propanamide;

3-(8-chloro-1,4-dihydro-4-methyl-1-phenyl-[1]-benzopyrano[4,3-c]pyrazol-3-yl)-2-cyano-3-oxo-N-benzyl-propanamide;

N-benzyl-2-cyano-3-(1,4-dihydro-4-methyl-1-phenyl-[1]-benzopyrano[4,3-c]pyrazol-3-yl)-3-oxo-propanamide;

N-butyl-3-[1-(4-chloro-phenyl)-1,4-dihydro-[1]-benzopyrano[4,3-c]pyrazol-3-yl]-2-cyano-3-oxo-propanamide;

N-tert.butyl-3-[1-(4-chloro-phenyl)-1,4-dihydro-[1]-benzopyrano[4,3-c]pyrazol-3-yl]-2-cyano-3-oxo-propanamide;

N-benzyl-3-[1-(3-chloro-phenyl)-1,4-dihydro-[1]-benzopyrano[4,3-c]pyrazol-3-yl]-2-cyano-3-oxo-propanamide;

3-[1-(4-chloro-phenyl)-1,4-dihydro-[1]-benzopyrano[4,3-c]pyrazol-3-yl]-2-cyano-N-cyclohexyl-3-oxo-propanamide;

3-(8-chloro-1,4-dihydro-1-phenyl-[1]-benzopyrano[4,3-c]pyrazol-3-yl)-2-cyano-N-(4-fluoro-phenyl)-3-oxo-propanamide; and 2-cyano-N-(4-fluoro-phenyl)-3-(1,4-dihydro-8-methoxy-1-phenyl-[1]-benzopyrano[4,3-c]pyrazol-3-yl)-3-oxo-propanamide.

EXAMPLE 14

3-(1,4-dihydro-1-phenyl-[1]-benzothiopyrano[4,3-c]pyrazol-3-yl)-3-oxo-propanenitrile (1.66 g) is reacted with phenyl isothiocyanate (1 g) in the presence of triethylamine (0.56 g) in dimethylformamide (15 ml) under stirring at 50° C. for 1 hour. After cooling, the reaction mixture is diluted with ice water and acidified to pH 1 with 2N HCl.

The precipitate is extracted with chloroform and the organic solution is washed with N HCl and then with water until neutral. After evaporation of the solvent in vacuo the residue is crystallized from CH₂Cl₂/isopropyl alcohol to give 1.55 g of 2-cyano-3-(1,4-dihydro-1-phenyl-[1]-benzothiopyrano[4,3-c]pyrazol-3-yl)-3-oxo-N-phenyl-thiopropanamide, m.p. 167°–170° C.

By proceeding analogously the following compounds can be prepared:

N-(4-chloro-phenyl)-2-cyano-3-(1,4-dihydro-1-phenyl-[1]-benzothiopyrano[4,3-c]pyrazol-3-yl)-3-oxo-thiopropanamide;

N-(4-chloro-phenyl)-2-cyano-3-(1,4-dihydro-1-phenyl-[1]-benzopyrano[4,3-c]pyrazol-3-yl)-3-oxo-thiopropanamide;

2-cyano-3-(1,4-dihydro-1-phenyl-[1]-benzopyrano[4,3-c]pyrazol-3-yl)-3-oxo-N-phenyl-thiopropanamide; and 3-(8-chloro-1,4-dihydro-1-phenyl-[1]-benzothiopyrano[4,3-c]pyrazol-3-yl)-2-cyano-3-oxo-N-phenyl-thiopropanamide.

EXAMPLE 15

1,4-Dihydro-1-phenyl-[1]-benzopyrano[4,3-c]pyrazole-3-carboxylic acid, ethyl ester (4.2 g) suspended in dioxane (60 ml) is heated with 1% KOH solution in ethanol (124 ml) at reflux temperature for 30 minutes. The reaction mixture is diluted with ice water and acidified to pH 3 with 37% HCl. The precipitate is filtered, washed with water and dried in vacuo at 50° C. to give 1,4-dihydro-1-phenyl-[1]-benzopyrano[4,3-c]pyrazole-3-carboxylic acid (3.5 g) which is reacted with thionyl chloride (1.34 ml) in dioxane (70 ml) at reflux temperature for 2 hours. After cooling the solution is evaporated to dryness in vacuo to give 1,4-dihydro-1-phenyl-[1]-benzopyrano[4,3-c]pyrazole-3-carbonyl chloride as crystalline residue. The crude product is dissolved in anhydrous dioxane (35 ml) and reacted for 2 hours under stirring at room temperature with ethyl cyanoacetate (1.5 g) carbanion, prepared by treatment with 50% sodium hydride (0.8 g) in anhydrous dimethylformamide (20 ml) at room temperature. The reaction mixture is then diluted with ice water and acidified to pH 1 with N HCl. The precipitate is filtered and dissolved in ethyl acetate, then the organic solution is washed with N HCl and water until neutral. Evaporation to dryness yields a residue which is purified over a SiO₂ column using chloroform/methanol 80:20 as eluent. Crystallization from acetone gives 1.2 g of 2-cyano-3-(1,4-dihydro-1-phenyl-[1]-benzopyrano[4,3-c]pyrazol-3-yl)-3-oxo-propanoic acid, ethyl ester.

By proceeding analogously the compound 2-cyano-3-(1,4-dihydro-1-phenyl-[1]-benzothiopyrano[4,3-c]pyrazol-3-yl)-3-oxo-propanoic acid, ethyl ester, m.p. 176°–178° C., can be obtained.

EXAMPLE 16

2-Cyano-3-(1,4-dihydro-1-phenyl-[1]-benzopyrano[4,3-c]pyrazol-3-yl)-3-oxo-propanoic acid, ethyl ester (1.2 g) is reacted with aniline (1.1 g) in xylene (100 ml) at the reflux temperature for 48 hours. After cooling the precipitate is filtered and washed with xylene, then crystallized from dichloromethane/methanol to give 0.7 g of 2-cyano-3-(1,4-dihydro-1-phenyl-[1]-benzopyrano[4,3-c]pyrazol-3-yl)-3-oxo-N-phenyl-propanamide, m.p. 280°–282° C.

By proceeding analogously the following compounds can be prepared:

N-(3-chloro-phenyl)-2-cyano-3-(1,4-dihydro-1-phenyl-[1]-benzopyrano[4,3-c]pyrazol-3-yl)-3-oxo-propanamide; and 2-cyano-3-(1,4-dihydro-1-phenyl-[1]-benzopyrano[4,3-c]pyrazol-3-yl)-3-oxo-N-(4-trifluoromethyl-phenyl)-propanamide.

EXAMPLE 17

2-Cyanoacetamide (1.85 g) is treated with 50% sodium hydride (1.28 g) in dimethylformamide (35 ml) under stirring at room temperature until the effervescence subsides. To this solution 1,4-dihydro-1-phenyl-[1]-benzothiopyrano[4,3-c]pyrazole-3-carbonyl chloride (6.53 g), prepared according to Example 15, dissolved in dioxane (35 ml) is added under stirring at room temperature. The reaction mixture is allowed to react for 2 hours, then is diluted with ice water and acidified to pH 1 with 37% HCl. The gummy precipitate is extracted with ethyl acetate and the organic solution washed with N HCl and then evaporated to dryness in vacuo. The residue is purified over $SiO_2$ column, using chloroform/methanol 80:20 as eluent, to give 2-cyano-3-(1,4-dihydro-1-phenyl-[1]-benzothiopyrano[4,3-c]pyrazol-3-yl)-3-oxo-propanamide, m.p. >300° C. dec., NMR (DMSO $d_6$) δ ppm: 4.10 (s) (2H, —S—$CH_2$—), 6.00–7.00 (bs) (2H, $CONH_2$), 6.60–7.80 (m) (9H, phenyl protons), 9.00 (bs) (1H, OH).

By proceeding analogously the following compound can be prepared:
2-cyano-3-(1,4-dihydro-1-phenyl-[1]-benzopyrano[4,3-c]pyrazol-3-yl-3-oxo-propanamide.

EXAMPLE 18

2-Cyano-3-(1,4-dihydro-1-phenyl-[1]-benzopyrano[4,3-c]pyrazol-3-yl)-3-oxo-N-phenyl-propanamide is dissolved by treatment with an equivalent amount of sodium ethoxide inethanol. The solution is evaporated to dryness and the residue is treated with isopropyl ether and then filtered to give the sodium salt of 2-cyano-3-[1,4-dihydro-1-phenyl-[1]-benzopyrano[4,3-c]pyrazol-3-yl]-3-oxo-N-phenyl-propanamide m.p. >300° C.

By proceeding analogously the sodium salts of the following compounds can be obtained:
2-cyano-3-(1,4-dihydro-1-phenyl-[1]-benzothiopyrano[4,3-c]pyrazol-3-yl)-3-oxo-N-phenyl-propanamide, m.p. >300° C.;
N-benzyl-2-cyano-3-(1,4-dihydro-1-phenyl-[1]-benzothiopyrano[4,3-c]pyrazol-3-yl)-3-oxo-propanamide, m.p. >290° C. dec.

EXAMPLE 19

Tablets, each weighing 150 mg and containing 50 mg of active substance, can be manufactured as follows:

| Composition (for 10 000 tablets) | |
|---|---|
| 2-cyano-3-(1,4-dihydro-1-phenyl-[1]-benzothiopyrano[4,3-c]pyrazol-3-yl)-3-oxo-N—phenyl-propanamide | 500 g |
| Lactose | 710 g |
| Corn starch | 238 g |
| Talc powder | 36 g |
| Magnesium stearate | 16 g |

2-cyano-3-(1,4-dihydro-1-phenyl-[1]-benzothiopyrano[4,3-c]pyrazol-3-yl)-3-oxo-N-phenyl-propanamide, lactose and half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

By proceeding analogously, tablets can be prepared having the same composition, but containing, for example, as active substance one of the following compounds:
2-cyano-3-(1,4-dihydro-1-phenyl-[1]-benzopyrano[4,3-c]pyrazol-3-yl)-3-oxo-N-phenyl-propanamide;
2-cyano-3-(1,4-dihydro-1-phenyl-[1]-benzothiopyrano[4,3-c]pyrazol-3-yl)-N-(4-fluoro-phenyl)-3-oxo-propanamide;
3-(8-chloro-1,4-dihydro-1-phenyl-[1]-benzothiopyrano[4,3-c]pyrazol-3-yl)-2-cyano-3-oxo-N-phenyl-propanamide;
N-benzyl-2-cyano-3-(1,4-dihydro-1-phenyl-[1]-benzopyrano[4,3-c]pyrazol-3-yl)-3-oxo-propanamide;
N-benzyl-2-cyano-3-(1,4-dihydro-1-phenyl-[1]-benzothiopyrano[4,3-c]pyrazol-3-yl)-3-oxo-propanamide;
N-(3-chloro-phenyl)-2-cyano-3-(1,4-dihydro-1-phenyl-[1]-benzothiopyrano[4,3-c]pyrazol-3-yl)-3-oxo-propanamide; and
N-benzyl-3-(8-chloro-1,4-dihydro-1-phenyl-[1]-benzothiopyrano[4,3-c]pyrazol-3-yl)-2-cyano-3-oxo-propanamide.

We claim:

1. A compound having the following general formula (I)

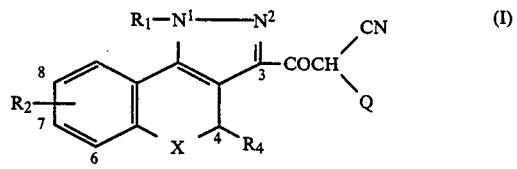

wherein
X represents an oxygen atom or a —$S(O)_n$-group, wherein n is zero, 1 or 2;
$R_1$ represents $C_1$–$C_6$ alkyl, benzyl, pyridyl or phenyl, the phenyl being unsubstituted or substituted by one or two substituents chosen independently from halogen, trifluoromethyl, $C_1$–$C_6$ alkyl, $C_1$–$C_6$ alkoxy, nitro, amino, formylamino and $C_2$–$C_8$ alkanoylamino;
each of $R_2$ and $R_3$ is independently:
(a) hydrogen, halogen or $C_1$–$C_6$ alkyl;
(b) hydroxy, $C_1$–$C_6$ alkoxy or $C_3$–$C_4$ alkenyloxy; or
(c) nitro, amino, formylamino or $C_2$–$C_8$ alkanoylamino;
$R_4$ represents hydrogen or $C_1$–$C_6$ alkyl; and
Q represents hydrogen, carboxy, $CONH_2$, $C_2$–$C_7$ alkoxycarbonyl or a

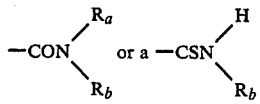

group, wherein $R_a$ represents hydrogen or $C_1$–$C_{20}$ alkyl and $R_b$ represents $C_1$–$C_{20}$ alkyl or a —$(CH_2)_m$—$R_5$ group, wherein m is zero, 1 or 2 and $R_5$ is:
(a') $C_5$–$C_8$ cycloalkyl;
(b') pyridyl, unsubstituted or substituted by one or two substituents chosen independently from halogen, $C_1$–$C_6$ alkyl and $C_1$–$C_6$ alkoxy; or
(c') phenyl, unsubstituted or substituted by one or two substituents independently chosen from halogen, $CF_3$, $C_1$–$C_6$ alkyl, $C_1$–$C_6$ alkoxy, amino, nitro, formylamino, $C_2$–$C_8$ alkanoylamino, di($C_1$–$C_6$ alkyl)amino, hydroxy, formyloxy and $C_2$–$C_8$ alkanoyloxy, and the pharmaceutically acceptable salts thereof.

2. A compound of formula (I) according to claim 1, wherein
X is oxygen or a —$S(O)_p$—group, in which p is zero or 1;

$R_1$ represents $C_1$–$C_6$ alkyl; unsubstituted pyridyl; or phenyl, unsubstituted or substituted by one or two substituents chosen independently from halogen, trifluoromethyl, $C_1$–$C_6$ alkyl, $C_1$–$C_6$ alkoxy, nitro, amino and $C_2$–$C_8$ alkanoylamino;

$R_2$ and $R_3$ each independently is hydrogen, halogen, $C_1$–$C_4$ alkyl or $C_1$–$C_4$ alkoxy;

$R_4$ represents hydrogen or $C_1$–$C_4$ alkyl;

Q represents hydrogen, —$CONH_2$, $C_2$–$C_5$ alkoxycarbonyl or a —$CONR'_aR'_b$ or —$CSNHR'_b$ group, wherein $R'_a$ is hydrogen or $C_1$–$C_6$ alkyl and $R'_b$ is $C_1$–$C_6$ alkyl or a —$(CH_2)_m$—$R'_5$ group wherein m is 0, 1 or 2 and $R'_5$ is $C_5$–$C_8$ cycloalkyl, unsubstituted pyridyl or phenyl unsubstituted or substituted by one or two substituents chosen independently from halogen, $CF_3$, $C_1$–$C_4$ alkyl, $C_1$–$C_4$ alkoxy, hydroxy, nitro and di-($C_1$–$C_4$ alkyl) amino; and the pharmaceutically acceptable salts thereof.

3. A compound of formula (I) according to claim 1, wherein

X is oxygen or sulphur;

$R_1$ represents $C_1$–$C_4$ alkyl or phenyl unsubstituted or substituted by one or two substituents selected independently from nitro, halogen, $CF_3$, $C_1$–$C_4$ alkyl and $C_1$–$C_4$ alkoxy; each of $R_2$ and $R_3$ independently is hydrogen, halogen, $C_1$–$C_4$ alkyl or $C_1$–$C_4$ alkoxy;

$R_4$ represents hydrogn or $C_1$–$C_4$ alkyl;

Q represents hydrogen, $C_2$–$C_3$ alkoxycarbonyl or a —$CONR''_aR''_b$ or —$CSNHR''_b$ group wherein $R''_a$ is hydrogen or $C_1$–$C_4$ alkyl and $R''_b$ is $C_1$–$C_4$ alkyl or a —$(CH_2)_m$—$R''_5$ group in which m is 0, 1 or 2 and $R''_5$ is $C_5$–$C_6$ cycloalkyl or it is phenyl unsubstituted or substituted by one or two substituents chosen independently from nitro, halogen, $CF_3$, $C_1$–$C_4$ alkyl and $C_1$–$C_4$ alkoxy and the pharmaceutically acceptable salts thereof.

4. A compound selected from the group consisting of:

2-cyano-3-(1,4-dihydro-1-phenyl)-[1]-benzothiopyrano[4,3-c]pyrazol-3-yl)-3-oxo-N-phenyl-propanamide;

N-(3-chloro-phenyl)-2-cyano-3-(1,4-dihydro-1-phenyl-[1]-benzothiopyrano[4,3-c]pyrazol-3-yl)-3-oxo-propanamide;

2-cyano-3-(1,4-dihydro-1-phenyl-[1]-benzothiopyrano[4,3-c]pyrazol-3-yl)-3-oxo-N-(3-trifluoromethyl-phenyl)-propanamide;

2-cyano-3-(1,4-dihydro-1-phenyl-[1]-benzothiopyrano[4,3-c]pyrazol-3-yl)-N-(4-fluoro-phenyl)-3-oxo-propanamide;

3-(8-chloro-1,4-dihydro-1-phenyl-[1]-benzopyrano[4,3-c]pyrazol-3-yl)-2-cyano-N-(4-fluoro-phenyl)-3-oxo-propanamide;

N-(3,5-dichloro-phenyl)-2-cyano-3-(1,4-dihydro-1-phenyl-[1]-benzothiopyrano[4,3-c]pyrazol-3-yl)-3-oxo-propanamide;

N-benzyl-2-cyano-3-(1,4-dihydro-1-phenyl-[1]-benzothiopyrano[4,3-c]pyrazol-3-yl)-3-oxo-propanamide;

3-(8-chloro-1,4-dihydro-1-phenyl-[1]-benzothiopyrano[4,3-c]pyrazol-3-yl)-2-cyano-3-oxo-N-phenyl-propanamide;

2-cyano-3-(1,4-dihydro-8-methyl-1-phenyl-[1]-benzothiopyrano[4,3-c]pyrazol-3-yl)-3-oxo-N-phenyl-propanamide;

N-benzyl-3-(8-chloro-1,4-dihydro-1-phenyl-[1]-benzothiopyrano[4,3-c]pyrazol-3-yl)-2-cyano-3-oxo-propanamide;

N-benzyl-2-cyano-3-(1,4-dihydro-8-methyl-1-phenyl-[1]-benzothiopyrano[4,3-c]pyrazol-3-yl)-3-oxo-propanamide;

2-cyano-3-(1,4-dihydro-8-methoxy-1-phenyl-[1]-benzothiopyrano[4,3-c]pyrazol-3-yl)-3-oxo-N-phenyl-propanamide;

N-(3-chloro-phenyl)-3-(8-chloro-1,4-dihydro-1-phenyl-[1]-benzothiopyrano[4,3-c]pyrazol-3-yl)-2-cyano-3-oxo-propanamide;

N-benzyl-2-cyano-3-(1,4-dihydro-8-methoxy-1-phenyl-[1]-benzothiopyrano[4,3-c]pyrazol-3-yl)-3-oxo-propanamide;

3-(8-chloro-1,4-dihydro-1-phenyl-[1]-benzothiopyrano[4,3-c]pyrazol-3-yl)-2-cyano-N-(4-fluoro-phenyl)-3-oxo-propanamide;

3-[1-(4-fluoro-phenyl)-1,4-dihydro-[1]-benzothiopyrano[4,3-c]pyrazol-3-yl]-2-cyano-N-(4-fluoro-phenyl)-3-oxo-propanamide;

3-[1-(3,5-dichloro-phenyl)-1,4-dihydro-[1]-benzothiopyrano[4,3-c]pyrazol-3-yl]-2-cyano-3-oxo-N-phenyl-propanamide;

2-cyano-3-[1,4-dihydro-1-(4-fluoro-phenyl)-[1]-benzothiopirano[4,3-c]pyrazol-3-yl]-3-oxo-N-phenyl-propanamide;

N-benzyl-3-[1-(3-chloro-phenyl)-1,4-dihydro-[1]-benzothiopyrano[4,3-c]pyrazol-3-yl]-2-cyano-3-oxo-propanamide;

N-benzyl-3-[1-(3,5-dichloro-phenyl)-1,4-dihydro-[1]-benzothiopyrano[4,3-c]pyrazol-3-yl]-2-cyano-3-oxo-propanamide;

N-benzyl-2-cyano-3-[1-(4-fluoro-phenyl)-1,4-dihydro-[1]-benzothiopyrano[4,3-c]pyrazol-3-yl]-3-oxo-propanamide;

N-benzyl-3-[8-chloro-1-(4-fluoro-phenyl)-1,4-dihydro-[1]-benzothiopyrano[4,3-c]pyrazol-3-yl]-2-cyano-3-oxo-propanamide;

3-[8-chloro-1-(4-fluoro-phenyl)-1,4-dihydro-[1]-benzothiopyrano[4,3-c]pyrazol-3-yl]-2-cyano-3-oxo-N-phenyl-propanamide;

2-cyano-3-(1,4-dihydro-1-phenyl-[1]-benzopyrano[4,3-c]pyrazol-3-yl)-3-oxo-N-phenyl-propanamide;

N-(3-chloro-phenyl)-2-cyano-3-(1,4-dihydro-1-phenyl[1]-benzopyrano[4,3-c]pyrazol-3-yl)-3-oxo-propanamide;

2-cyano-3-(1,4-dihydro-1-phenyl-[1]-benzopyrano[4,3-c]pyrazol-3-yl)-N-(4-fluoro-phenyl)-3-oxo-propanamide;

N-benzyl-2-cyano-3-(1,4-dihydro-1-phenyl-[1]-benzopyrano[4,3-c]pyrazol-3-yl)-3-oxo-propanamide;

2-cyano-3-(1,4-dihydro-1-phenyl-[1]-benzothiopyrano[4,3-c]pyrazol-3-yl)-N-(3-fluoro-phenyl)-3-oxo-propanamide;

3-[1-(3-chloro-phenyl)-1,4-dihydro-[1]-benzopyrano[4,3-c]pyrazol-3-yl]-2-cyano-3-oxo-N-phenyl-propanamide;

2-cyano-3-[1,4-dihydro-1-(4-fluoro-phenyl)-[1]-benzopyrano[4,3-c]pyrazol-3-yl]-3-oxo-N-phenyl-propanamide;

N-benzyl-3-[1-(3-chloro-phenyl)-1,4-dihydro-[1]-benzopyrano[4,3-c]pyrazol-3-yl]-2-cyano-3-oxo-propanamide;

N-benzyl-2-cyano-3-[1-(4-fluoro-phenyl)-1,4-dihydro-[1]-benzopyrano[4,3-c]pyrazol-3-yl]-3-oxo-propanamide;

2-cyano-3-(1,4-dihydro-4-methyl-1-phenyl-[1]-benzopyrano[4,3-c]pyrazol-3-yl)-3-oxo-N-phenyl-propanamide;

N-benzyl-2-cyano-3-(1,4-dihydro-4-methyl-1-phenyl-[1]benzopyrano[4,3-c]pyrazol-3-yl)-3-oxo-propanamide;

3-(8-chloro-1,4-dihydro-1-phenyl-[1]-benzopyrano[4,3-c]pyrazol-3-yl)-2-cyano-3-oxo-N-phenyl-propanamide;

N-benzyl-3-(8-chloro-1,4-dihydro-1-phenyl-[1]-benzopyrano[4,3-c]pyrazol-3-yl)-2-cyano-3-oxo-propanamide;

3-(8-chloro-1,4-dihydro-1-phenyl-[1]-benzothiopyrano[4,3-c]pyrazol-3-yl)-2-cyano-N-(3-fluoro-phenyl)-3-oxo-propanamide;

3-(8-chloro-1,4-dihydro-1-phenyl-[1]-benzopyrano[4,3-c]pyrazol-3-yl)-2-cyano-N-(3-fluoro-phenyl)-3-oxo-propanamide, and the pharmaceutically acceptable salts thereof.

5. A pharmaceutically acceptable salt of a compound of claim 4, wherein the salt is the sodium or potassium salt.

6. A pharmaceutical composition for treating bacterial or viral infections in mammals, comprising an anti-bacterial or anti-viral effective amount of a compound according to claim 1, or a pharmaceutically acceptable salt thereof, in association with a suitable carrier or diluent.

7. A method of treating bacterial or viral infections in a mammal in need of such treatment, which comprises administering to said mammal an anti-bacterial or anti-viral effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 4,816,467
DATED : March 28, 1989  Page 1 of 2
INVENTOR(S) : DORIA et al It is certified that error appears in the above-identified patent and that said Letters Patent is hereby corrected as shown below:

On the cover page, the formula in the abstract should appear as follows:

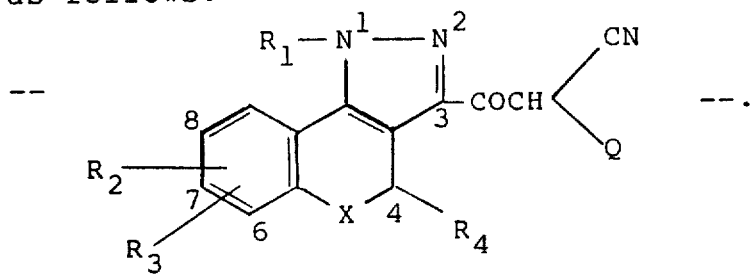

Column 1, lines 12 to 20, the formula should appear as follows:

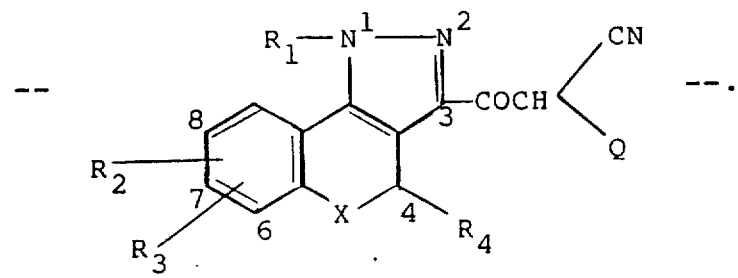

Column 4, line 55, "[4,3-c]pyrazol-3-yl]-3-yl]" should read --[4,3-c]pyrazol-3-yl]--.

Column 5, lines 42 and 43, "wherein Q is an Q defined above, except carboxy, so obtaining a compound of formula (I), wherein Q is as" should read --wherein Q' is as defined above, except carboxy, so obtaining a compound of formula (I), wherein Q' is as--.

UNITED STATES PATENT AND TRADEMARK OFFICE
CERTIFICATE OF CORRECTION

PATENT NO. :  4,816,467
DATED      :  March 28, 1989
INVENTOR(S):  DORIA et al

It is certified that error appears in the above-identified patent and that said Letters Patent is hereby corrected as shown below:

Column 26, lines 20 to 28, Formula (I) of Claim 1 should appear as follows:

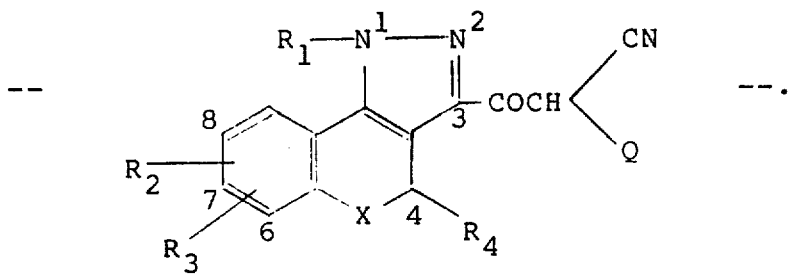

Signed and Sealed this

Sixth Day of March, 1990

Attest:

JEFFREY M. SAMUELS

Attesting Officer    Acting Commissioner of Patents and Trademarks